US008551726B2

(12) United States Patent
Morimoto et al.

(10) Patent No.: US 8,551,726 B2
(45) Date of Patent: Oct. 8, 2013

(54) METHOD OF MODULATING HSF-1

(75) Inventors: Richard I. Morimoto, Evanston, IL (US); Sandy Westerheide, Evanston, IL (US); Julius Anckar, Turku (FI); Lea Sistonen, Turku (FI); Barbara Calamini, Chapel Hill, NC (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/155,170

(22) Filed: Jun. 7, 2011

(65) Prior Publication Data

US 2011/0311508 A1    Dec. 22, 2011

Related U.S. Application Data

(63) Continuation of application No. PCT/US2009/067118, filed on Dec. 8, 2009.

(60) Provisional application No. 61/120,542, filed on Dec. 8, 2008, provisional application No. 61/221,315, filed on Jun. 29, 2009.

(51) Int. Cl.
*C12Q 1/34* (2006.01)

(52) U.S. Cl.
USPC .......................................................... 435/18

(58) Field of Classification Search
USPC ................... 435/18, 375; 536/24.1
See application file for complete search history.

(56) References Cited

U.S. PATENT DOCUMENTS

| 7,345,178 | B2 | 3/2008 | Nunes et al. | |
|---|---|---|---|---|
| 2005/0250794 | A1 | 11/2005 | Napper et al. | |
| 2006/0014705 | A1 | 1/2006 | Howitz et al. | |
| 2006/0074124 | A1 | 4/2006 | Napper et al. | |
| 2006/0229265 | A1 | 10/2006 | Milburn et al. | |
| 2007/0043050 | A1 | 2/2007 | Nunes et al. | |
| 2007/0065890 | A1 | 3/2007 | Reinberg et al. | |
| 2007/0238682 | A1* | 10/2007 | Nudler et al. | 514/44 |
| 2008/0021063 | A1 | 1/2008 | Kazantsev | |
| 2008/0207724 | A1 | 8/2008 | Mink et al. | |
| 2008/0214800 | A1 | 9/2008 | Navia et al. | |
| 2008/0234223 | A1 | 9/2008 | Yang et al. | |
| 2008/0255382 | A1 | 10/2008 | Andrus et al. | |
| 2009/0012080 | A1 | 1/2009 | Bemis et al. | |
| 2009/0022694 | A1 | 1/2009 | Distefano | |
| 2009/0075948 | A1* | 3/2009 | Parker | 514/159 |
| 2009/0092600 | A1* | 4/2009 | Kufe | 424/133.1 |
| 2010/0279311 | A1* | 11/2010 | Kimura | 435/7.1 |

FOREIGN PATENT DOCUMENTS

| EP | 1839656 A1 | 10/2007 |
|---|---|---|
| EP | 2014281 A1 | 1/2009 |
| WO | 2005026112 A2 | 3/2005 |
| WO | WO 2005/060711 * | 7/2005 |
| WO | 2006078941 A2 | 7/2006 |
| WO | 2006094209 A2 | 9/2006 |
| WO | 2006094210 A2 | 9/2006 |
| WO | 2006094233 A1 | 9/2006 |
| WO | 2006094235 A1 | 9/2006 |
| WO | 2006094236 A1 | 9/2006 |
| WO | 2006094237 A2 | 9/2006 |
| WO | 2006094246 A2 | 9/2006 |
| WO | 2006094248 A1 | 9/2006 |
| WO | 2007019344 A1 | 2/2007 |
| WO | 2007019345 A1 | 2/2007 |
| WO | 2007019346 A1 | 2/2007 |
| WO | 2007019416 A1 | 2/2007 |
| WO | 2007019417 A1 | 2/2007 |
| WO | 2007084162 A2 | 7/2007 |
| WO | 2008019825 A1 | 2/2008 |
| WO | 2008082646 A2 | 7/2008 |
| WO | 2008086400 A2 | 7/2008 |
| WO | 2008091710 A2 | 7/2008 |
| WO | 2008128155 A2 | 10/2008 |
| WO | 2008156869 A2 | 12/2008 |
| WO | 2009015179 A1 | 1/2009 |
| WO | 2009015180 A2 | 1/2009 |

OTHER PUBLICATIONS

Erkine A. et al. Dynamic Chromatin Alterations Triggered by Natual and Synthetic Activation Domains J of Biological Chemistry 278(10)7755-7764, Mar. 2003.*
Yang X. et al. Lysine Acetylation Molecular Cell 31:449-460, Aug. 22, 2008.*
Morimoto R. Proteotoxic Stress and Inducible Chaperone Networks . . . Genes & Development 22:1427-1438, 2008.*
Shi, Y., et al., "Molecular chaperones as HSF1-specific transcriptional repressors," Genes & Development, 12: 654-666 (1998).
Balch, W. E., et al., "Adapting Proteostasis for Disease Intervention," Science, 319: 916-919 (2008).
Morimoto, R., "Protein Misfolding in Neurodegenerative Disease," Slide presentation at the Philip Hauge Abelson Advancing Science Seminar Science, Stress, and Human Health, Oct. 24, 2008.
Morley, J. F., et al., "Regulation of Longevity in *Caenorhabditis elegans* by Heat Shock Factor and Molecular Chaperones," Molecular Biology of the Cell, 15: 657-664 (2004).
Szczepankiewicz, B. G., et al., "Sirtuin Modulators: Targets for Metabolic Diseases and Beyond," Current Topics in Medicinal Chemistry, 8: 1533-1544, (2008).
Putics, A. et al., "Resveratrol induces the heat-shock response and protects human cells from severe heat stress," Antioxidants & Redox Signaling, 10(1): 65-75 (2008).
Trott, A. et al., "Activation of heat shock and antioxidant responses by the natural product celastrol: Transcriptional signatures of a thiol-targeted molecule," Molecular Biology of the Cell, American Society for Cell Biology, 19(3): 1104-1112 (2008).
Westerheide, S. D. et al., "Celastrols as inducers of the heat shock response and cytoprotection," The Journal of Biological Chemistry, 279(53): 56053-56060 (2004).
Liu, Ying, et al., "Screen selection of target genes regulated by HSF1 in heat shock response from myocardium of gene knockout mice," Journal of Central South University, No. 1, vol. 29 (Dec. 31, 2004).
Ding, Haipeng, et al., "Research Progress in pharmacologic molecular targets of celastrol," Chinese Journal of Pharmacology and Toxicology, No. 4, vol. 26, (Aug. 21, 2012).

* cited by examiner

*Primary Examiner* — Ralph Gitomer
(74) *Attorney, Agent, or Firm* — Casimir Jones, S.C.

(57) ABSTRACT

The present invention is directed to methods of modulating HSF1 activity comprising modifying the acetylation of the DNA binding domain of the HSF1.

21 Claims, 26 Drawing Sheets

A

B

C

METHOD OF MODULATING HSF-1

RELATED APPLICATIONS

This application is a continuation of International Application No. PCT/US09/67118, which designated the United States and was filed on Dec. 8, 2009, published in English, which claims the benefit of U.S. Provisional Application No. 61/120,542, filed Dec. 8, 2008 and U.S. Provisional Application No. 61/221,315, filed Jun. 29, 2009. The entire teachings of the above applications are incorporated herein by reference.

GOVERNMENT SUPPORT

This invention was made with government support under grants AG026647 and GM038109 awarded by the National Institutes of Health. The Government has certain rights in the invention.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., *Nature* 426: 891-894, 2003; Ron et al., *Nat Rev Mol Cell Biol* 8: 519-529, 2007]. The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., *Cell* 131: 809-821, 2007]. Metabolic enzymes also influence cellular protein folding efficiency because the organic and inorganic solutes produced by a given compartment effect polypeptide chain salvation through non-covalent forces, including the hydrophobic effect, that influences the physical chemistry of folding. Metabolic pathways produce small molecule ligands that can bind to and stabilize the folded state of a specific protein, enhancing folding by shifting folding equilibria [Fan et al., *Nature Med.*, 5, 112 (January 1999); Hammarstrom et al., *Science* 299, 713 (2003)]. Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., *Nature* 426: 905-909, 2003]. Human gain of function diseases are similarly frequently the result of a disruption in protein homeostasis leading protein aggregation [Balch et al. (2008), *Science* 319: 916-919].

At the cellular level, the heat shock response protects cells against a range of acute and chronic stress conditions [Westerheide et al., *J Biol. Chem.* 280(39): 33097 (2005)]. The heat shock response (HSR) is a genetic response to environmental and physiological stressors resulting in a repression of normal cellular metabolism and a rapid induction of heat shock protein (HSP) genes expressing molecular chaperones, proteases and other proteins that are useful for protection and recovery from cellular damage as a result of protein misfolding and aggregation [Westerheide et al.]. The heat shock response is mediated by the transcription factor, heat shock factor-1 (HSF-1). Although the HSR protects cells against damage caused by various stressors, accumulation of large amounts of HSPs can be detrimental for cell growth and division [Morimoto et al. (1998), *Genes Dev.* 12, 3788].

Both dysfunction in proteostasis and the heat shock response have been implicated in a diverse range of diseases including for example, cancer, neurodegenerative disease, metabolic diseases, inflammatory disease and cardiovascular disease. There remains a need in the art for therapeutic approaches to treat conditions associated with proteostasis dysfunction and/or altered induction of heat shock proteins.

SUMMARY OF THE INVENTION

The present invention is based on the discovery that cellular HSF1 activity is modulated by the acetylation state of its DNA binding domain. For example, Example 1 shows that activation of SIRT1 (which inhibits HSF1 acetylation) prolongs HSF1 DNA binding to the hsp70 promoter by maintaining HSF1 in a deacetylated state whereas downregulation of SIRT1 accelerates attenuation of HSF1 activity.

In one embodiment, the invention is a method of modulating the activity of heat shock transcription factor 1 (HSF1) in a cell comprising modifying the acetylation of a lysine residue in the DNA binding domain of the HSF1. In another embodiment, the activity of HSF1 is increased by inhibiting the acetylation of a lysine residue. In yet another embodiment, the activity of the HSF1 is decreased by promoting the acetylation of a lysine residue. The lysine residue can be lysine 80 (HSF1 K80) of human HSF1 or a corresponding conserved amino acid in a non-human HSF1.

In another embodiment, the acetylation of HSF1 is inhibited by administering to the cell an agent that inhibits acetylation of a lysine residue in the DNA binding domain of HSF1. In some aspects, the agent that inhibits the acetylation of the lysine residue is an isolated sirtuin, a sirtuin activating agent or a histone acetyltransferase (HAT) inhibiting agent.

In some aspects, the acetylation of HSF1 is inhibited by administering to the cell an effective amount of an isolated sirtuin or a sirtuin activating agent. An isolated SIRT1 or a SIRT1 activating agent can be administered.

In yet another embodiment, the acetylation of HSF1 is inhibited by administering to the cell a HAT inhibitor.

In another embodiment, the acetylation of HSF1 is promoted by administering to the cell a sirtuin inhibiting agent, such as a SIRT1 inhibiting agent or HAT activating agent.

In an additional embodiment, the invention is a method of increasing the activity of HSF1 in a subject in need thereof comprising inhibiting the acetylation of HSF1 in a subject. In one embodiment, the subject is a human.

In another embodiment, the invention is a method of decreasing the activity of HSF1 in a subject in need thereof comprising promoting the acetylation of HSF1 in a subject. In one embodiment, the subject is a human.

In a further embodiment, the invention is a method of treating a patient suffering from a condition associated with a dysfunction in the homeostasis of a protein comprising administering to said patient a therapeutically effective amount of an agent that inhibits acetylation of HSF1. In one embodiment, the condition is a loss of function disorder. In another embodiment, the condition is a gain of function disorder. In another embodiment, the agent that inhibits acetylation of HSF1 is an isolated sirtuin, a sirtuin activating agent or HAT inhibiting agent. In a further embodiment, the agent is an isolated SIRT1 or a SIRT1 activating agent. In an additional embodiment, the agent is a HAT inhibiting agent.

In another embodiment, the invention is method of treating a patient suffering from a condition associated with increased expression of a heat shock protein comprising administering to said patient a therapeutically effective amount of an agent that promotes acetylation of HSF1. In one embodiment, the condition is cancer or a tumor. In another embodiment, the condition is a viral infection. In another embodiment, the agent that promotes acetylation of HSF1 is a sirtuin inhibiting agent or a HAT activating agent. In a further embodiment, the agent is a SIRT1 inhibiting agent.

The invention additionally encompasses methods of increasing a heat shock response and of treating a disease of proteostasis dysfunction in a patient in need thereof comprising administering to said patient an effective amount of a heat shock activator and an effective amount of an agent that inhibits acetylation of HSF1. In another embodiment, the invention is a pharmaceutical composition comprising a heat shock activator and an agent that inhibits acetylation of HSF1.

The invention also encompasses a method of identifying an agent that modulates HSF1 activity in a cell comprising administering a test agent to a cell; and monitoring the acetylation of a lysine residue within the DNA binding domain of the HSF1; wherein a change in the acetylation of the DNA binding domain relative to that in the absence of the test agent indicates that the test agent modulates HSF1 activity in the cell. In a further embodiment, the acetylation of HSF1 K80 or a corresponding conserved amino acid is monitored.

In another embodiment, the invention is a method of identifying an agent that modulates HSF1 activity in a cell comprising administering a test agent to a cell or cell lysate and measuring the acetylation of a sirtuin substrate; wherein a change in the acetylation of the substrate relative to the acetylation in the absence of the test agent indicates that the test agent modulates HSF1 activity in the cell. In one embodiment, the sirtuin is SIRT1.

In a further embodiment, the invention is a method of identifying an agent that modulates HSF1 activity in a cell comprising administering a test agent to a cell or cell lysate and measuring the acetylation of a histone acetyltransferase (HAT) substrate; wherein a change in the acetylation of the substrate relative to the acetylation in the absence of the test agent indicates that the test agent modulates HSF1 activity in the cell.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 5:
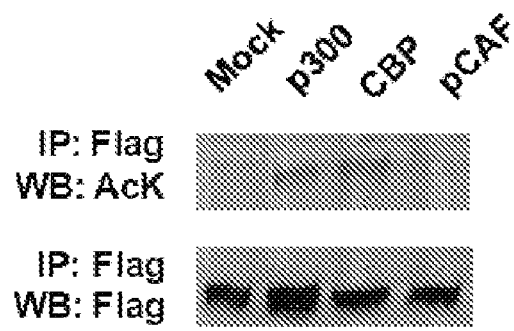
Figure 5:
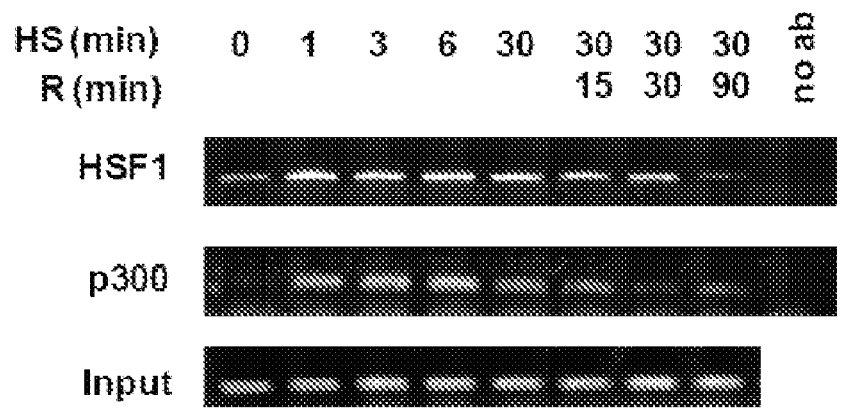
Figure 5:
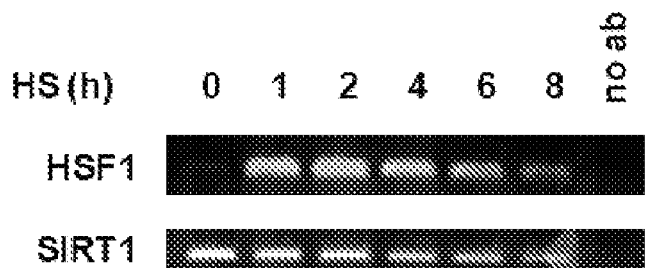

FIG. 5A: p300 and CBP, but not pCAF, induce HSF1 acetylation. 293T cells were transfected with Flag-HSF1 and p300, CBP, or pCAF, treated with HS and analyzed by acetylation assay.

FIG. 5B: p300 binds to the hsp70 promoter in vivo. Chromatin immunoprecipitation experiments performed at the indicated 42° C. heat shock timepoints with and without the indicated recovery timepoints at 37° C. show p300 binding to the hsp70 promoter. Chromatin was crosslinked, harvested, and immunoprecipitated with an antibody specific for p300 or HSF1. The samples were then analyzed by PCR with primers specific for the hsp70.1 promoter. Reactions were also performed using 1% of input and using no antibody. Upon heat shock, HSF1 and p300 are both recruited within one minute to the hsp70 promoter, and binding gradually attenuates during the recovery timepoints.

FIG. 5C: SIRT1 binds to the hsp70 promoter in vivo. Chromatin immunoprecipitation experiments performed at the indicated 42° C. heat shock timepoints show SIRT1 binding to the hsp70 promoter. Chromatin was crosslinked, harvested, and immunoprecipitated with an antibody specific for HSF1 or SIRT1. The samples were then analyzed by PCR with primers specific for the hsp70 promoter. Control reactions were also performed using no antibody. SIRT1 binds to the hsp70 promoter under both basal and heat shock conditions.

Figure 6:
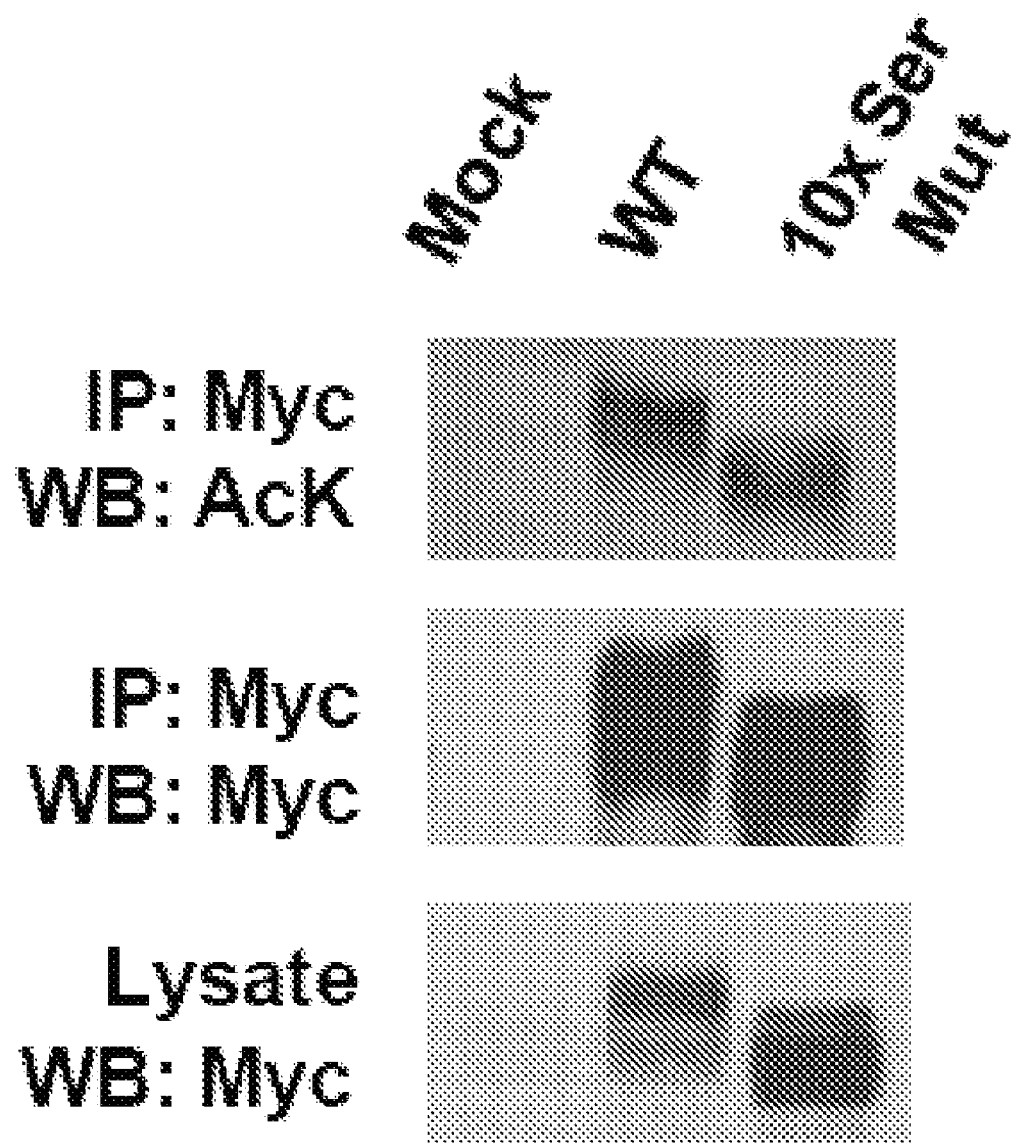

FIG. 6: Bulk HSF1 phosphorylation in not a prerequisite for acetylation. 293T cells were cotransfected with Myc-HSF1 WT or a ten serine phosphomutant of HSF1 together with p300. Twenty-four hours after transfection, cells were treated with a one hour heat shock at 42° C. Cell lysates were subjected to immunoprecipitation and acetylated HSF1 was detected using western blotting. Myc antibody was used to detect total HSF1.

Figure 7:
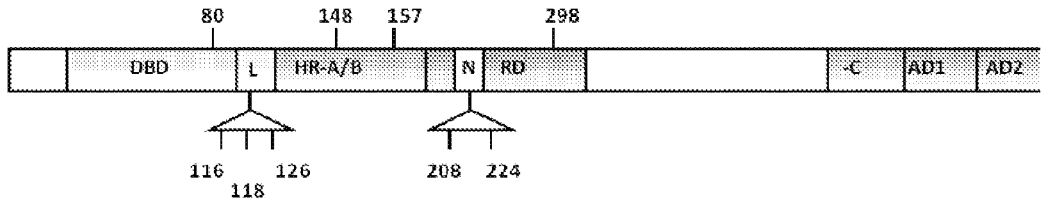
Figure 7:
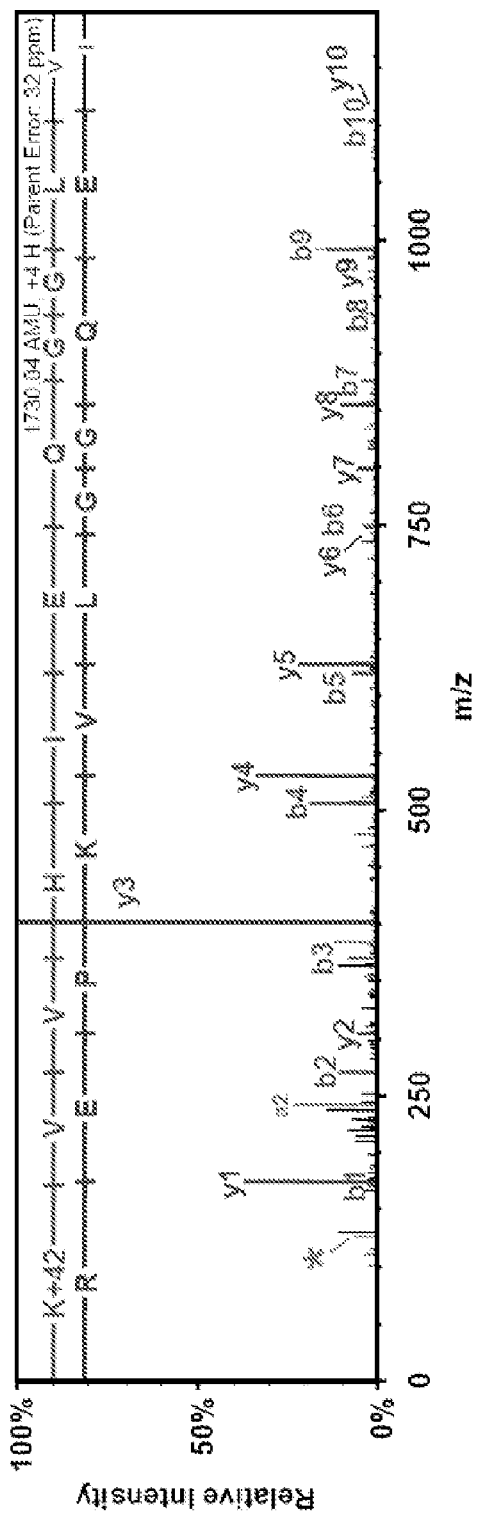
Figure 7:
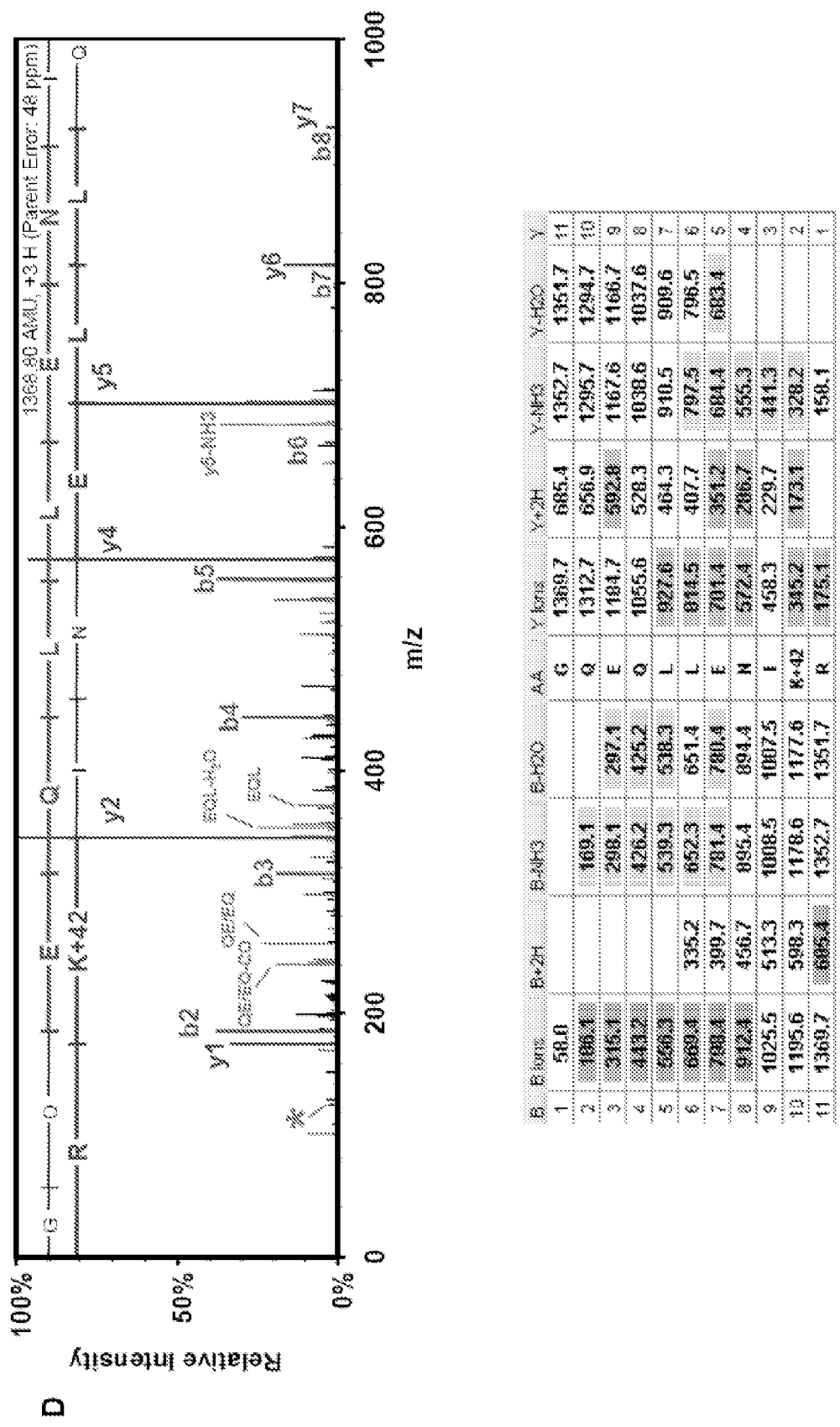
Figure 7:
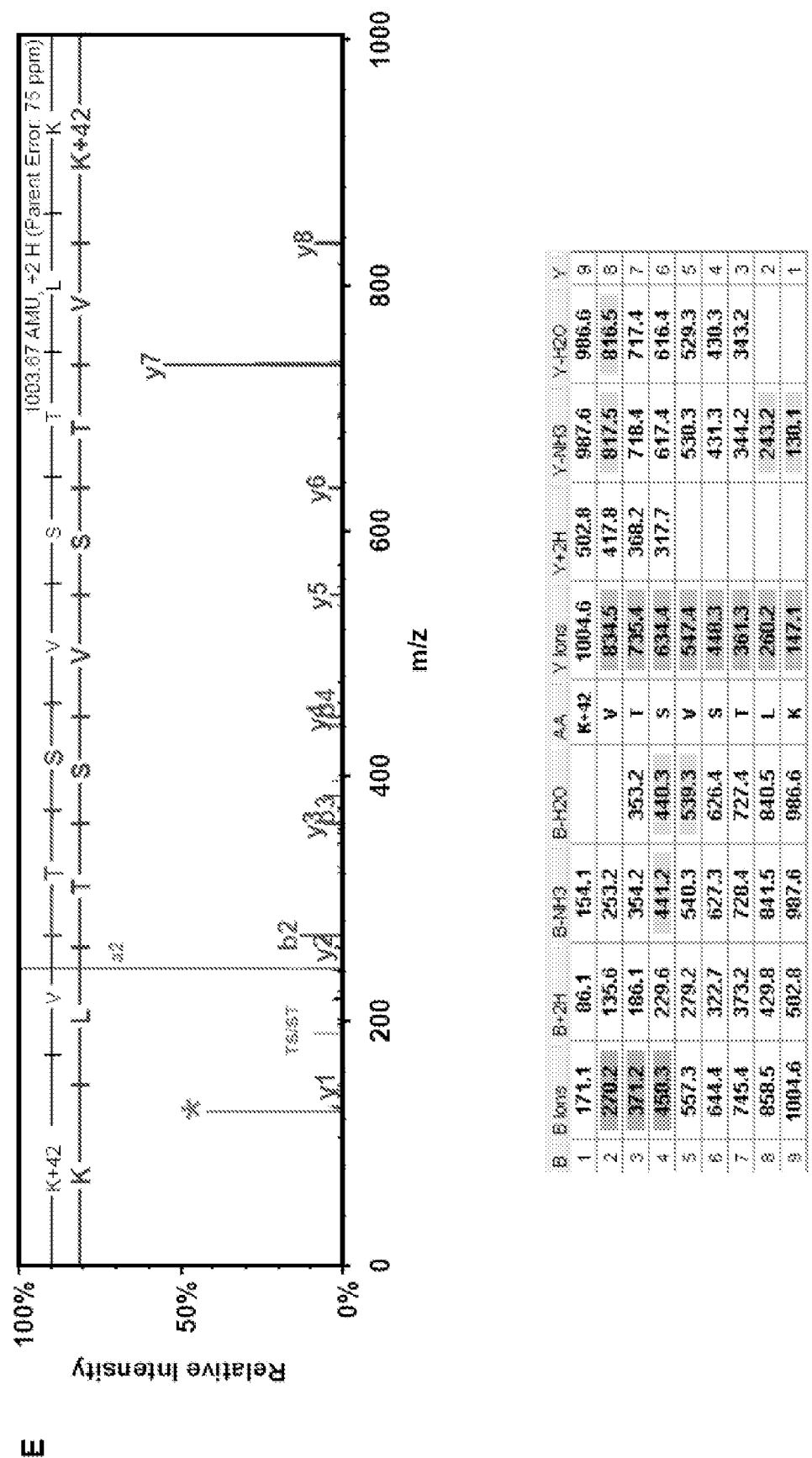
Figure 7:
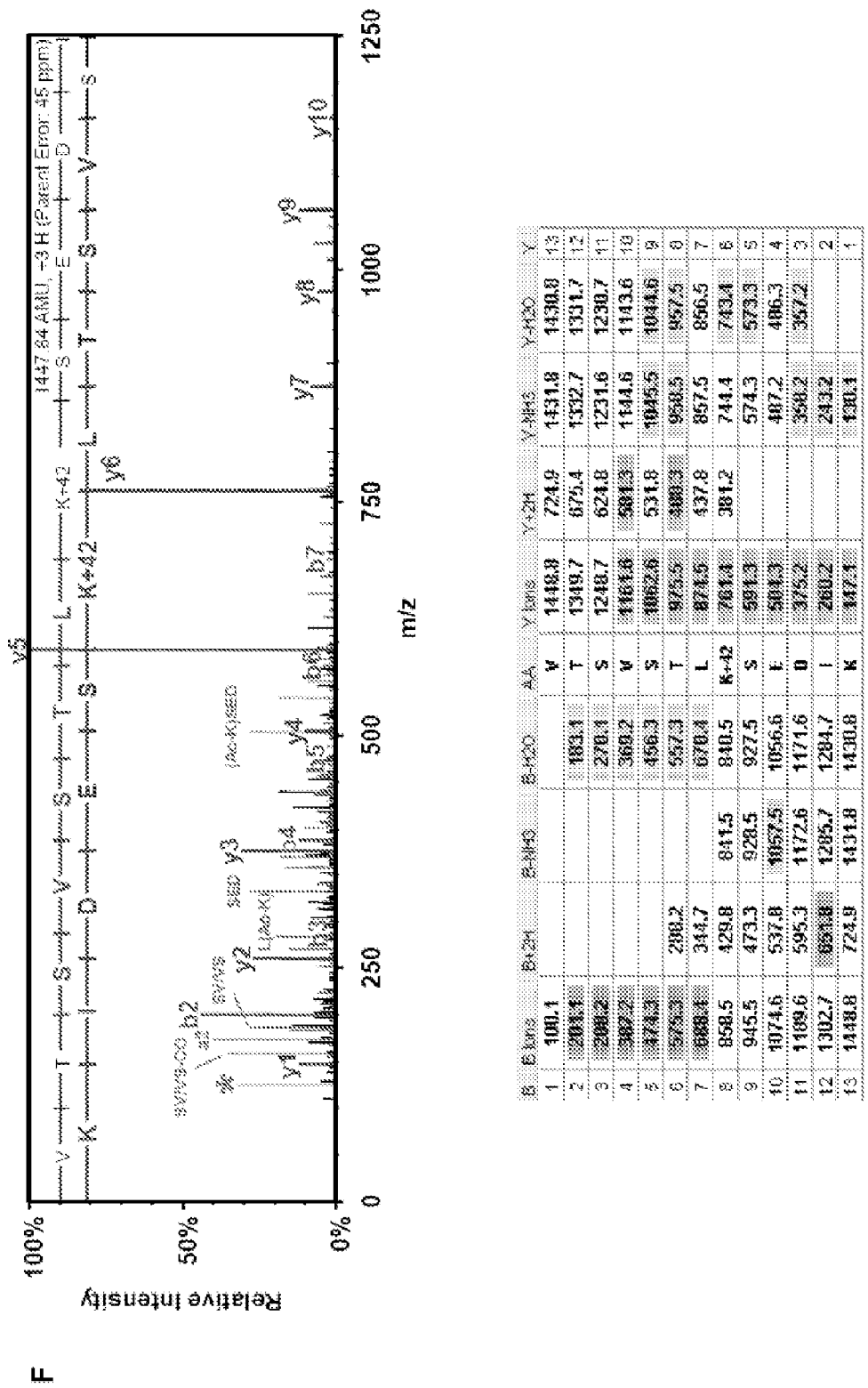
Figure 7:
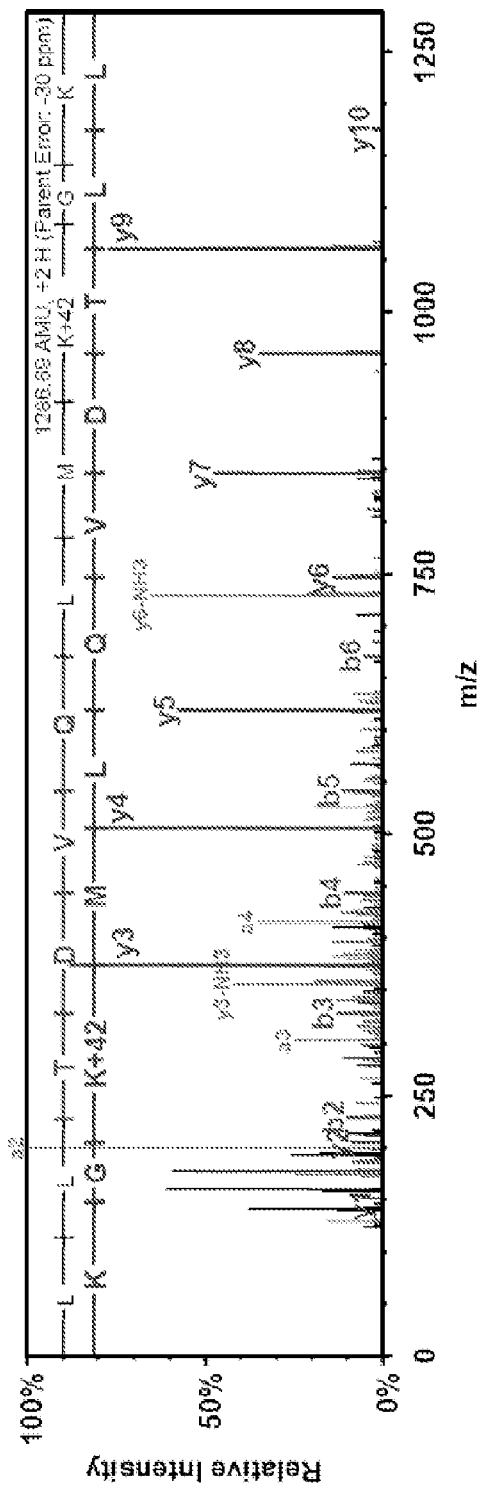
Figure 7:
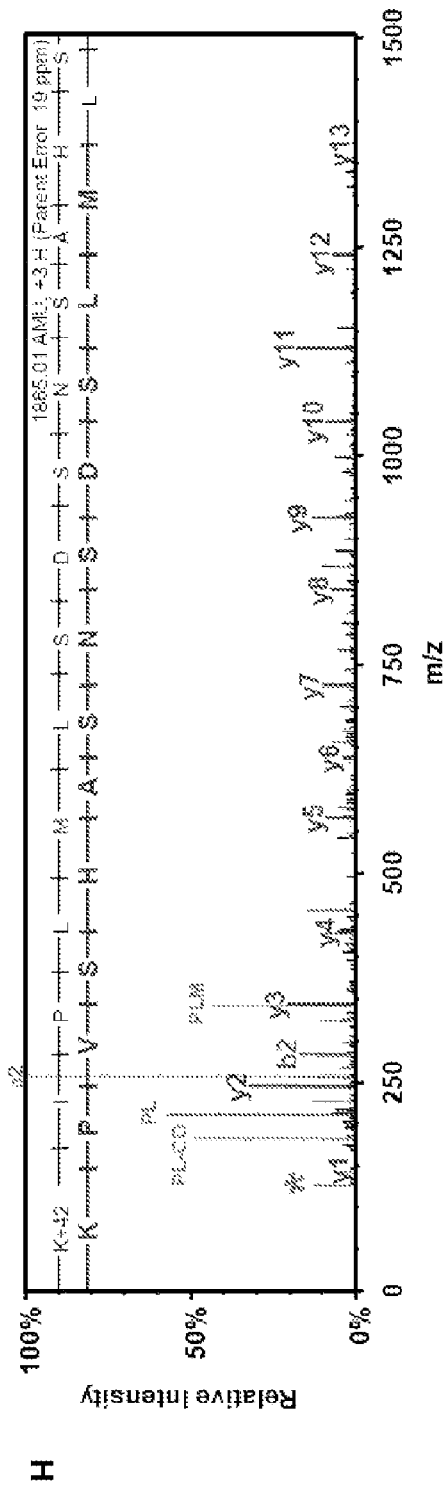
Figure 7:
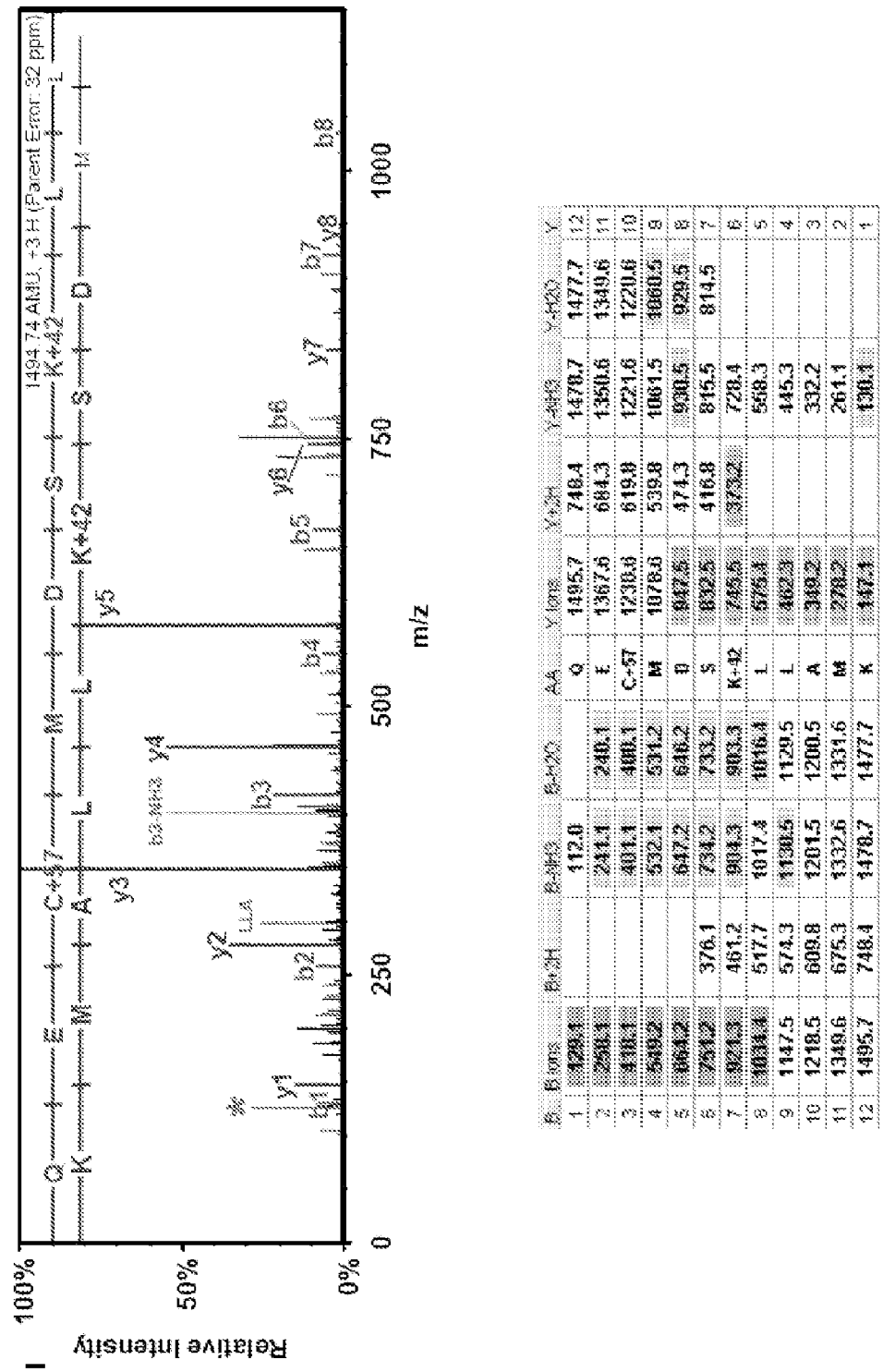
Figure 7:
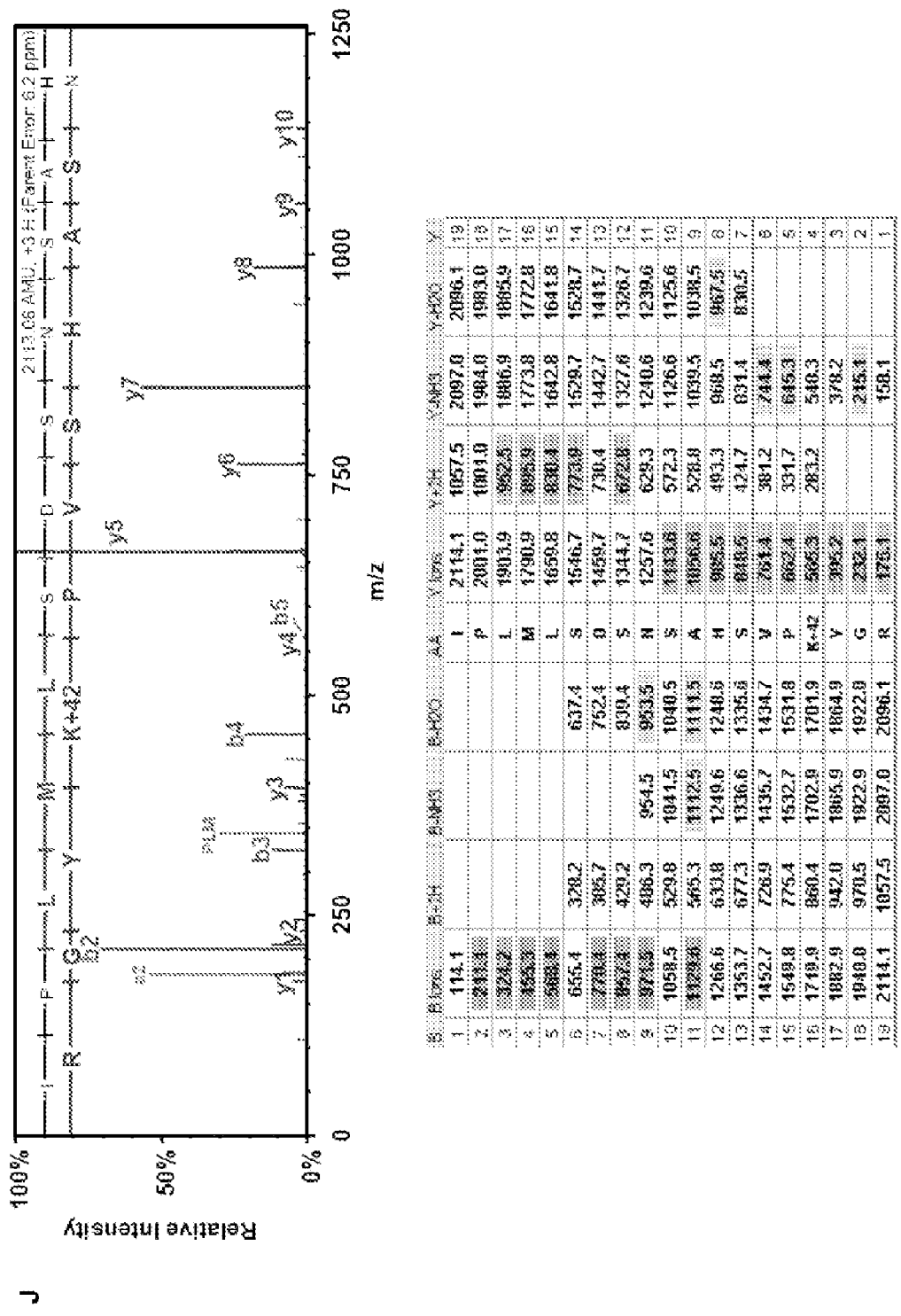
Figure 7:
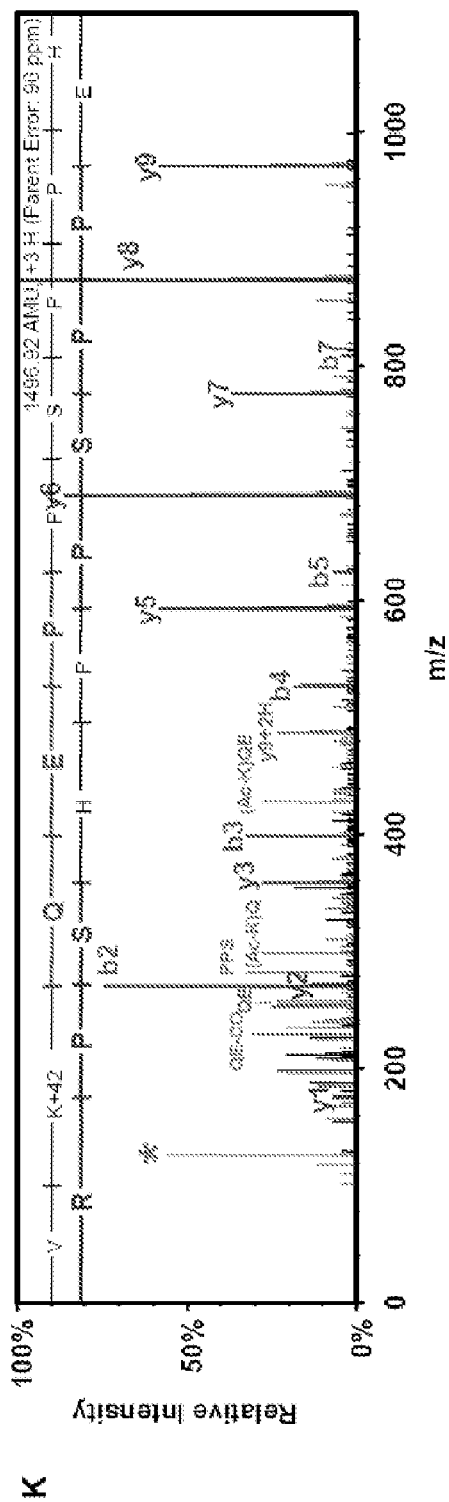

FIG. 7A: HSF1 can be acetylated on nine lysines. Flag-HSF1, which was expressed and purified from 293T cells that had been cotransfected with p300 and subjected to either heat shock (42° C., 1 hour) or celastrol treatment (5 µM, 1 hour) and analyzed by LC-MS/MS. Positions of the identified acetylated lysine residues within murine HSF1 are shown. DBD, DNA-binding domain; L, linker region; HR-A/B and -C, heptad repeat domains; RD, regulatory domain; N, nuclear localization sequence; AD1 and AD2, activation domains.

FIG. 7B: Acetylated lysines are conserved. Sequence alignment of the acetylated lysines across multiple species was performed using T-COFFEE version 5.13. The acetylated lysines are shown in red, and amino acid numbers are indicated to the right. Hs, *Homo sapiens* (NP_005517); Mm, *Mus musculus* (NP_032322); Dr, *Danio rerio* (NP_571675); Xl, *Xenopus laevis* (NP_001084036.1); Dm, *Drosophila melanogaster* (P22813); Ce, *Caenorhabditis elegans* (NM_060630); Sc, *Saccharomyces cerevisiae* (P10961).

FIG. 7C-7K: Mass spectrometry data for the nine acetylated sites within HSF1. MS/MS spectra were extracted and analyzed using the Mascot and Scaffold programs assuming digestion with trypsin. For each acetylated tryptic peptide identified, the mass spectrum generated from fragmentation of the HSF1-derived precursor ion is shown in the upper panel, and the corresponding fragment ion coverage is displayed in the lower panel. Acetylation is indicated by an additional mass of 42 Daltons. A low-mass ion at m/z 126 representing the acetylated lysine immonium ion minus NH3 was identified in most MS/MS spectra (labeled with asterisk) and used as further validation for acetylation (12).

Figure 8:
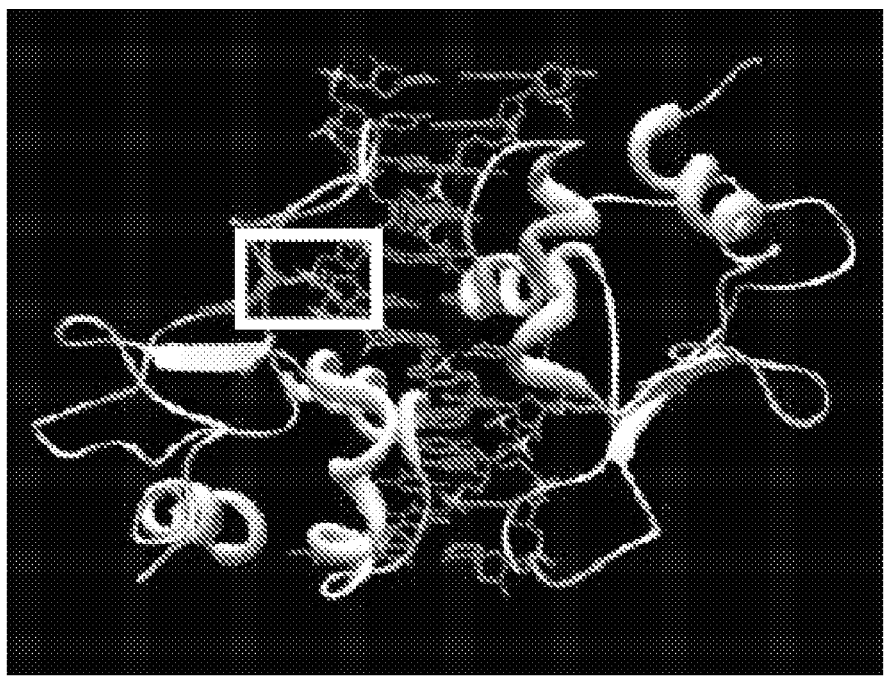
Figure 8:
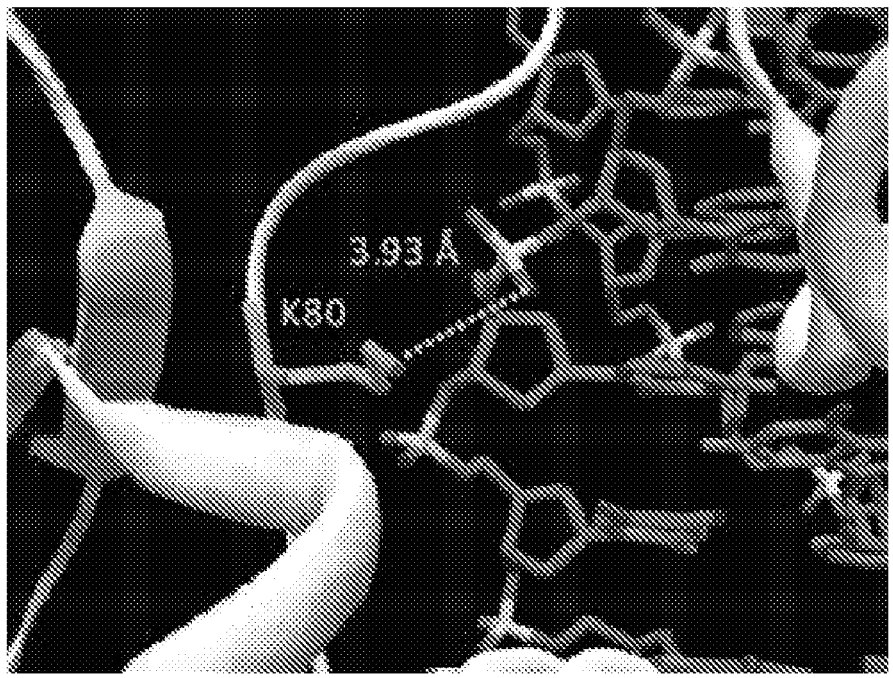

FIG. 8: Using the coordinates supplied with the crystal structure of the *K. lactis* HSF DNA-binding domain complexed with an HSE (13), we threaded the aligned sequence of human HSF1 using Swiss Model. The side chain of K80 and the distance to the DNA phosphate backbone are shown in green. The boxed area in the upper panel is shown at a higher magnification in the lower panel.

Figure 9:
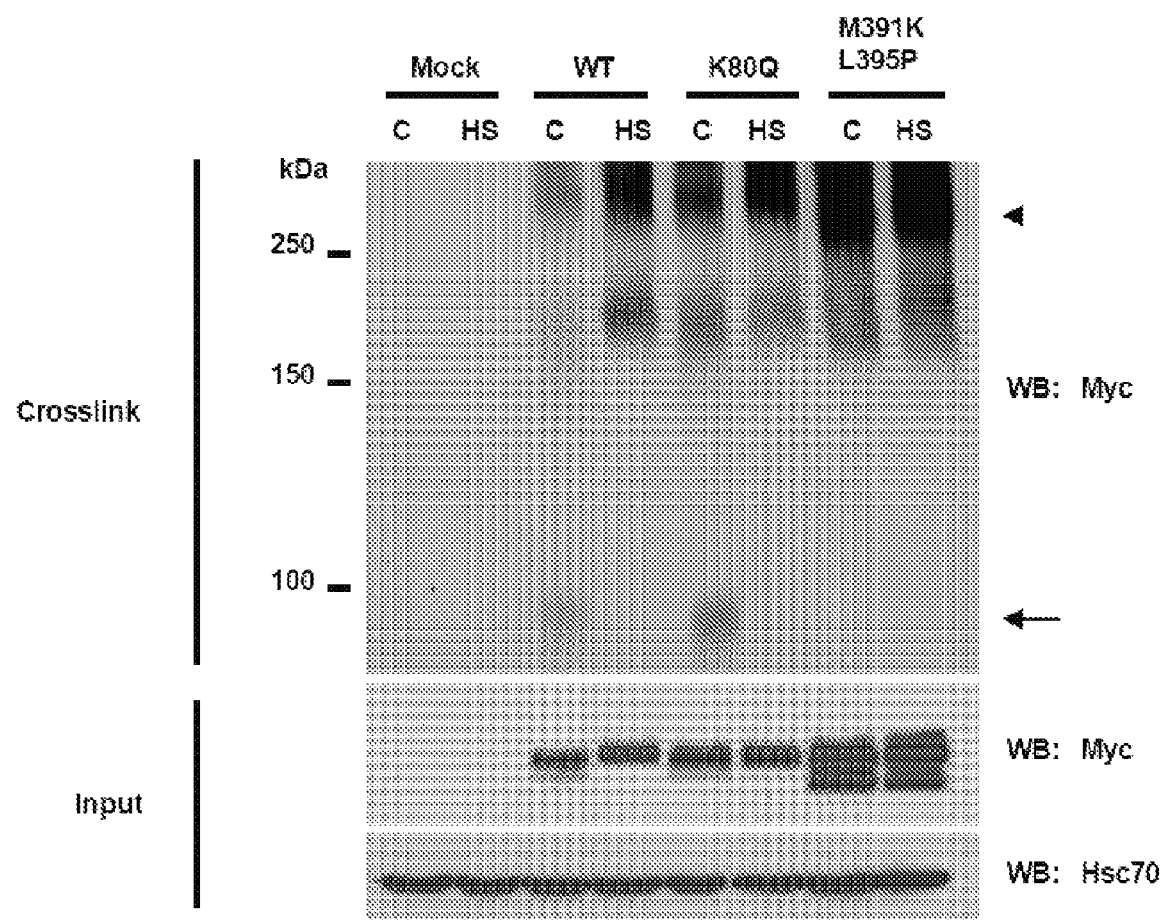

FIG. 9: The HSF1 K80Q mutant is not defective in trimerization ability. A prerequisite of stable HSF binding to DNA is the formation of trimeric HSF complexes. Therefore, it is conceivable that mutations of K80 disrupted proper HSF1 folding or the stress-induced formation of HSF trimers. To explore this possibility, e a cross-linking assay was used to determine the formation of higher-order complexes upon heat shock. K562 cells were transfected with WT Myc-HSF1, Myc-HSF1 K80Q or Myc-HSF1 M391K, L395P, a previously characterized HSF1 mutant that is constitutively trimeric (14). Cells were treated with or without heat shock (HS, 42° C., 20 minutes) followed by treatment with the EGS crosslinking agent. Protein extracts were separated by SDS-PAGE and western blot analysis was performed with the indicated antibodies. The arrow indicates monomeric HSF1 and the arrowhead marks trimeric HSF1. Both WT and K80Q HSF1 underwent a monomer-to-trimer transition in response to heat shock, demonstrating that the mutations did not affect HSF1 trimerization.

Figure 10:
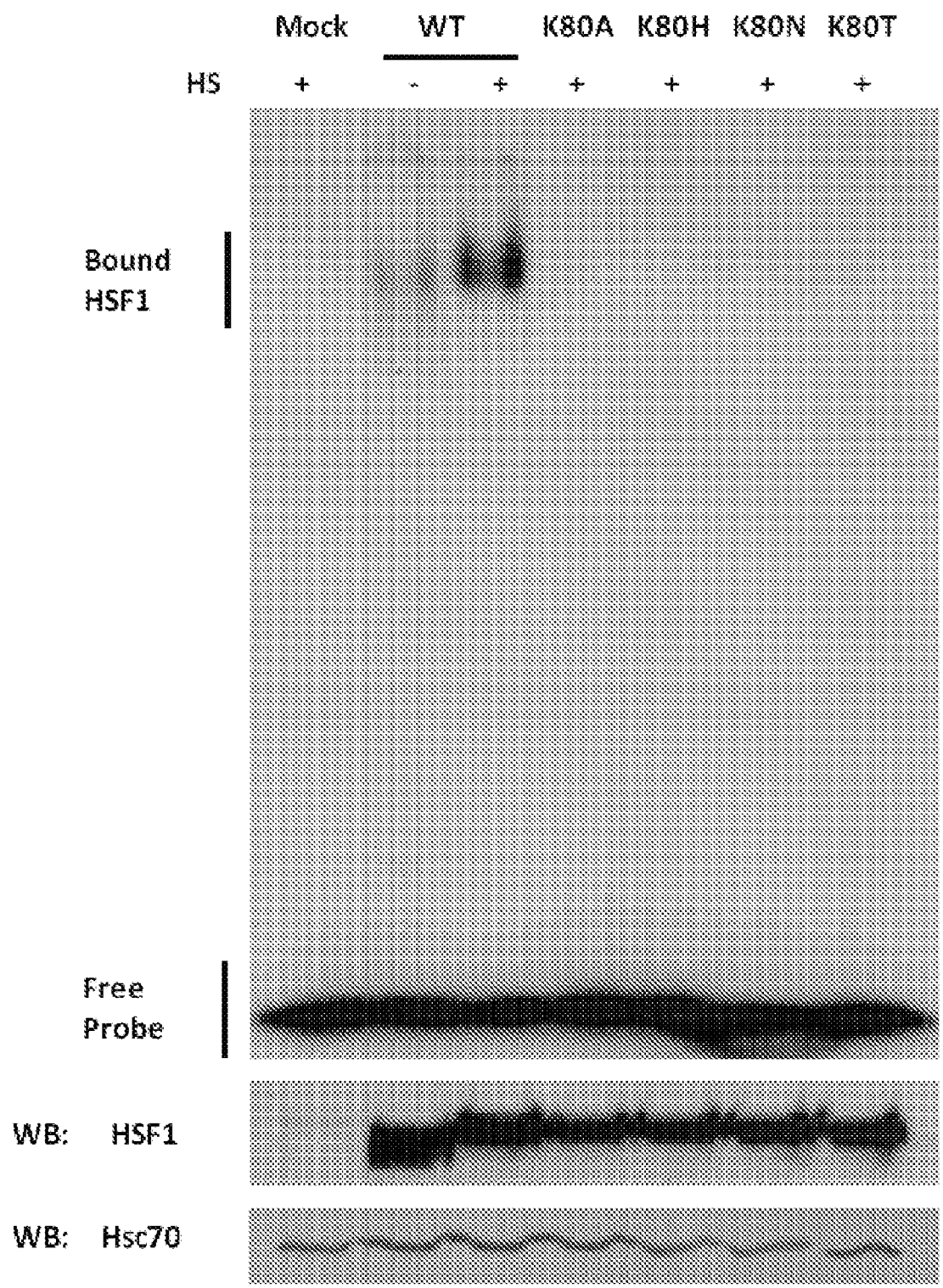

FIG. 10: HSF1 DNA binding requires a lysine at residue 80. EMSA reactions in hsf1−/− cells transfected with the indicated HSF1 construct and treated with or without heat shock (HS, 42° C. 20 minutes) are shown. The oligonucleotide used as a probe contains the proximal HSE from the human hsp70 promoter. Western blot analysis was performed on the same samples to show HSF1 and Hsc70 expression levels. Hsc70 is shown for equal loading. Mutation of K80 to A, H, N and T all interfered with the ability of HSF1 to bind to DNA upon heat shock.

Figure 11:
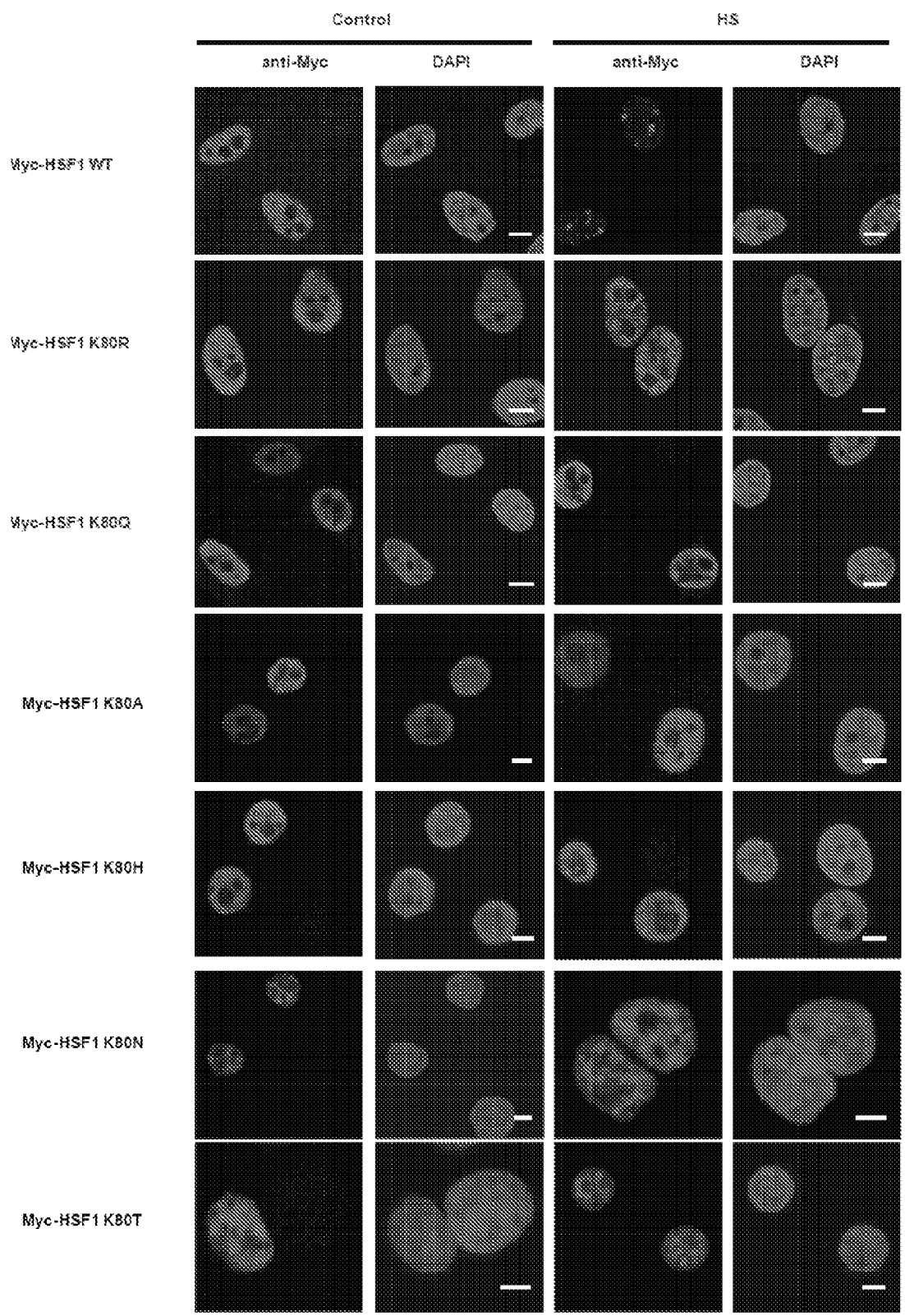

FIG. 11: The formation of nuclear stress bodies requires a lysine at residue 80 of HSF1. Confocal images of HeLa cells transfected with the indicated versions of Myc-HSF1 and treated with or without a one hour 42° C. heat shock (HS) are shown. Exogenous HSF1 was stained using an α-Myc antibody (red) and DNA was stained using DAPI (blue). Bar=5 µm. Mutation of HSF1 K80 to R, Q, A, H, N and T all impaired the ability of HSF1 to relocalize into characteristic nuclear stress bodies upon heat shock.

Figure 12:
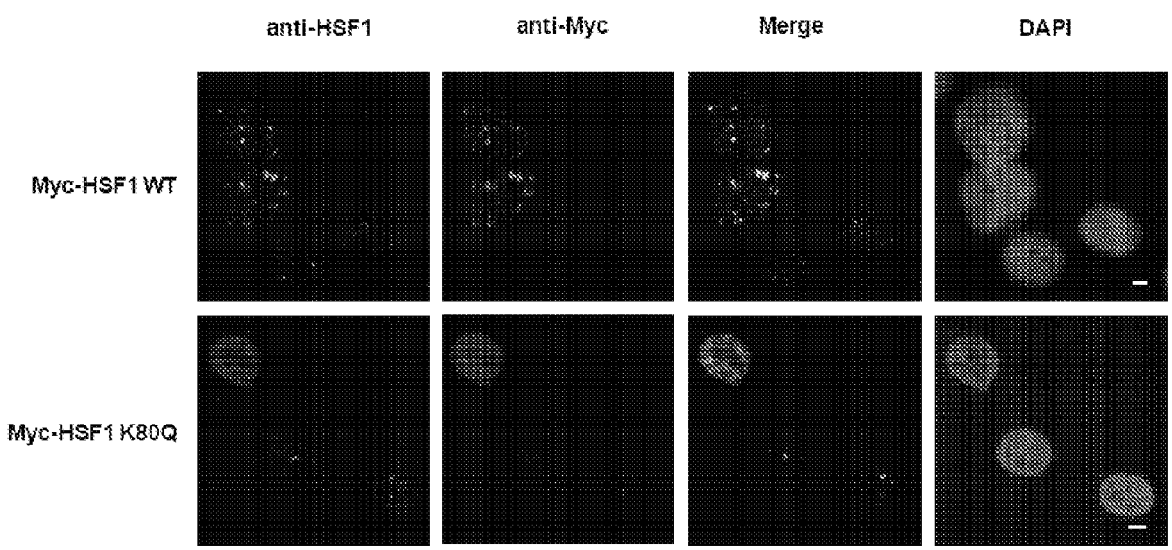

FIG. 12: HSF1 K80Q functions in a dominant-negative fashion. Stable HSF1 binding to an HSE requires the simultaneous contact of three DNA-binding domains to three nGAAn repeats. As acetylation of one or two monomers could disrupt the binding of associated non-modified monomers, a small population of acetylated HSF1 DNA-binding domains is likely to have dominant negative effects. To investigate this issue, we transfected HeLa cells with WT or the K80Q mutant of Myc-HSF1 and double-stained the cells with antibodies against HSF1 or Myc to analyze the ability of endogenous HSF1 to form nSBs. Shown are confocal images of HeLa cells transfected with the indicated versions of Myc-HSF1 and treated with or without heat shock (HS, 42° C., 1 hour). HSF1 proteins were stained using antibodies against HSF1 (green) and Myc (red). DNA was stained using DAPI (blue). Bar=5 µm. Whereas endogenous and exogenous WT HSF1 colocalized in nSBs upon heat shock, no nSBs could be detected with either antibody in cells expressing the K80Q mutant of HSF1. Therefore, it is likely that the biological implications of K80 acetylation might be greater than the actual levels of K80-acetylated HSF1 molecules.

Figure 13:
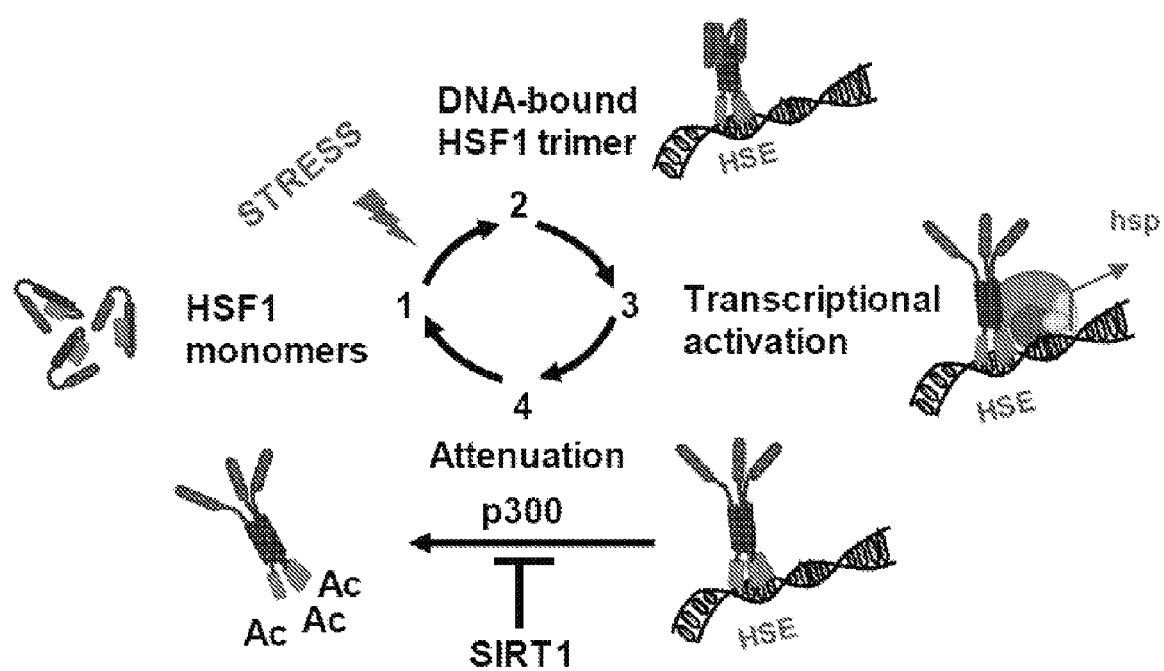

FIG. 13: Model of the HSF1 activation cycle. Step 1: HSF1 in the resting state is an inert monomer that can be cytoplasmic or nuclear. Step 2: Upon stress, HSF1 forms DNA-binding homotrimers that bind to HSEs. Step 3: HSF1 acquires transcriptional activity. Step 4: HSF1 transcriptional activity is abrogated during attenuation. Attenuation has two regulated steps, including negative feedback from hsp expression that represses the transactivation function of DNA-bound HSF1 (not shown) and inhibition of DNA binding via acetylation of the DNA-binding domains of HSF1. SIRT1 regulates the attenuation phase of the HSR through prevention of HSF1 acetylation.

Figure 14:
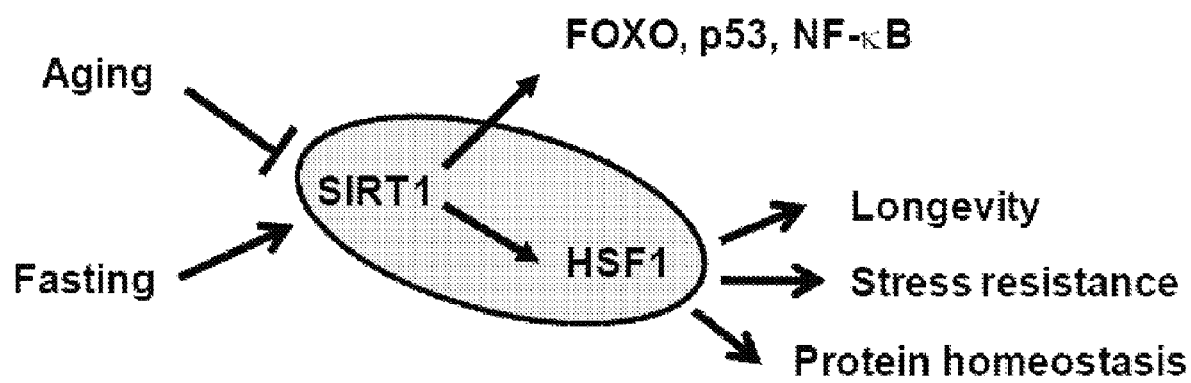

FIG. 14: Model of HSF1—SIRT1 regulatory network. The regulation of SIRT1 by aging and cellular metabolic state affects the activity of a network of transcription factors including HSF1 to result in increased longevity and stress resistance.

Figure 15:
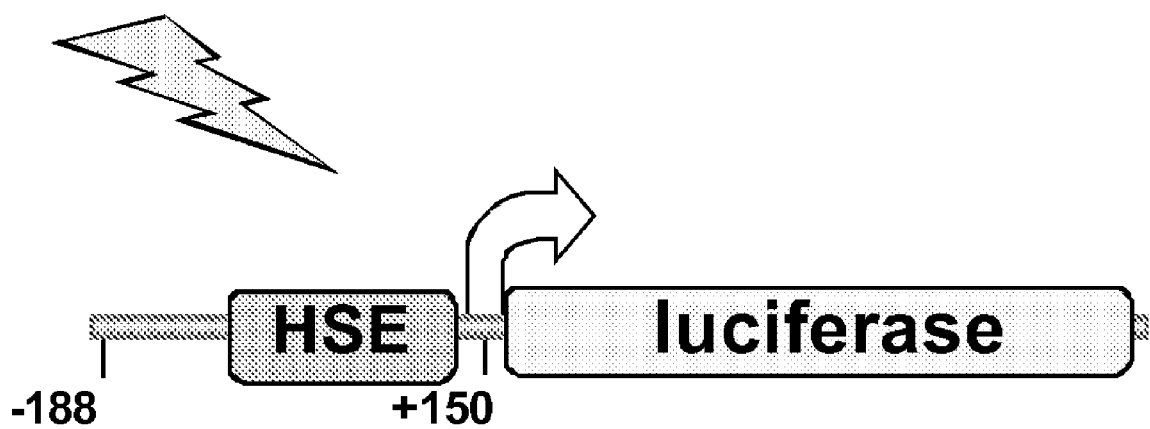

FIG. 15 is a drawing depicting the hsp70 promoter reporter; the hsp70.1pr-luc HeLa stable cell line contains hsp70.1 promoter sequence from −188 to +150 and includes the proximal heat shock element (HSE).

Figure 16:
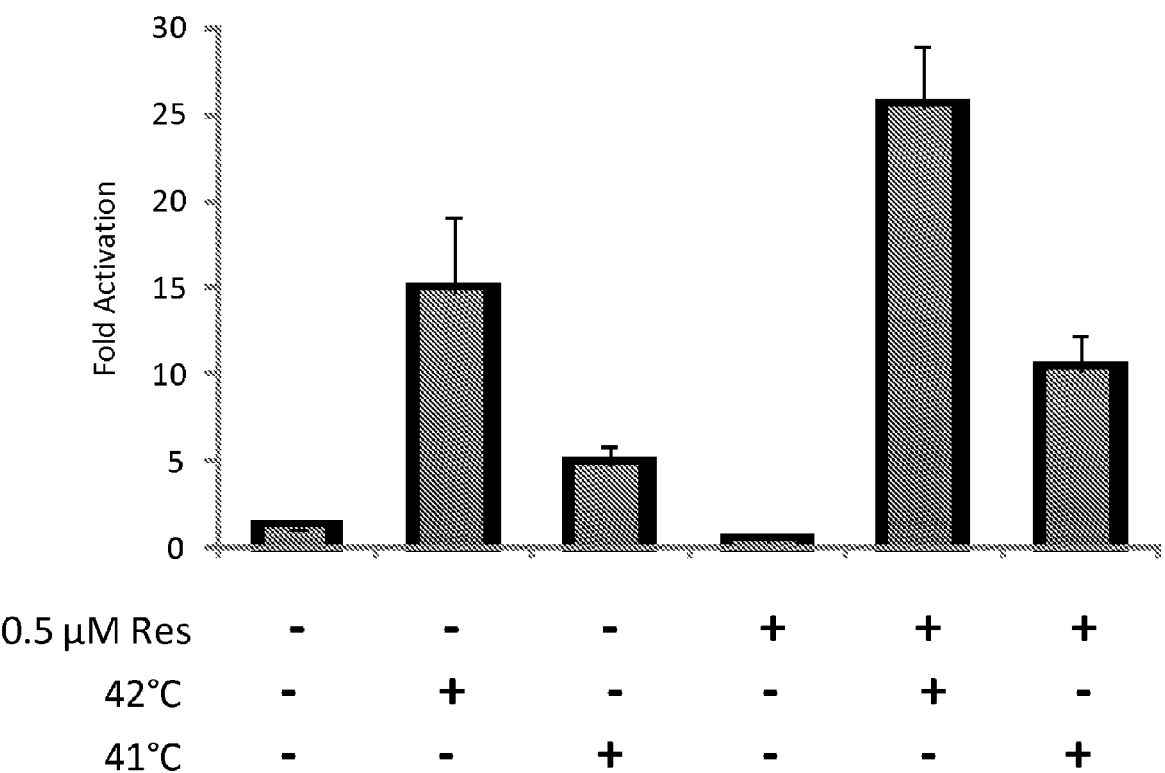

FIG. 16 is a bar graph showing fold activation of HeLa hsp70.1pr-luc cells treated with or without resveratrol and either a 41° C. heat shock or a 42° C. heat shock as indicated prior to luciferase analysis.

Figure 17:
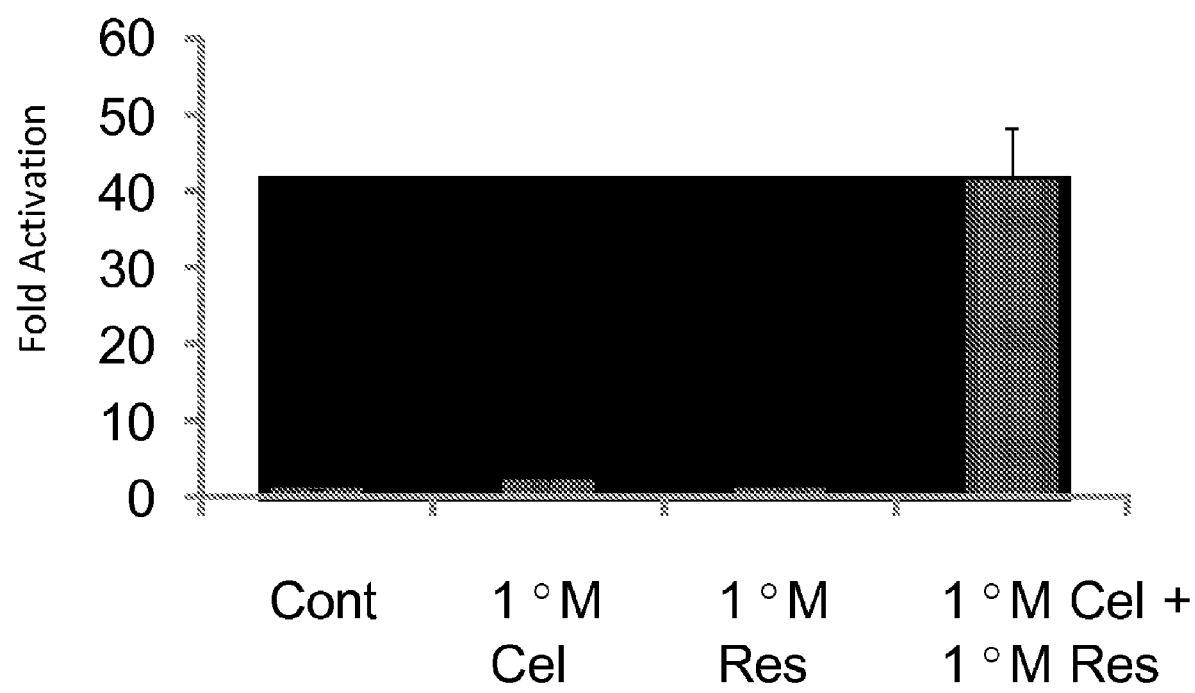

FIG. 17 is a bar graph showing fold activation of HeLa hsp70.1pr-luc cells treated with celastrol and/or resveratrol as indicated prior to luciferase analysis.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

The terms "heat shock factor," "heat shock transcription factor" and "HSF" refer to a family of transcription factors which are involved in stress-inducible gene expression. At least four members of the HSF family have been described in vertebrates and plants. *Drosophila* and *C. Elegans* express only one HSF. (Wu, *Ann. Rev. Cell Dev. Biol.* 1995; 11:441-469). In human cells, three HSFs (HSF1, HSF2, and HSF4) have been characterized (Morimoto, et al., *Genes Dev.* 1998; 12:3788-3796). HSF1 is ubiquitously expressed and plays the principal role in the stress-induced expression of HSPs.

The sequence of HSF1 is highly conserved among species. The DNA-binding domain of HSF1 is greater than 100 amino acids long and is located near the N-terminus. There is about 70% homology between the DNA binding domain of human HSF1 and *Drosophila* HSF and there is about 55% homology between human HSF1 and *S. cerevisiae* HSF. In human HSF1, the DNA binding domain extends from amino acid residue 13 to amino acid residue 121. As used herein, the term "HSF1" encompasses HSF1 from any species or cell type and also encompasses HSF from *Drosophila* and *C. elegans*. Such HSF and HSF1 proteins possess a lysine for acetylation within the DNA binding domain which corresponds to HSF1 K80. The term "non-human HSF1" denotes HSF1 from a non-human species. The terms HSF1 includes but is not limited to peptides having the amino acid sequences of GenBank Acc. Nos. NP_005517, NP_032322, NP_571675, NP_001084036.1, P22813, NM_060630 and P10961.

In one embodiment, the HSF1 is mammalian HSF1. In another embodiment, the HSF1 is human HSF1. In one embodiment, the HSF1 has an amino acid sequence that has at least about 85%, 90%, 95%, 98% and 99% sequence identity to GenBank Acc. No. NP_005517 (SEQ ID NO:1). In another embodiment, the HSF1 has the amino acid sequence of GenBank Acc. No. NP_005517.

The terms "sequence identity" or "identity" in reference to a sequence refers to sequence identity between two amino acid sequences or between two nucleotide sequences. Identity can each be determined by comparing a position in each sequence which may be aligned for purposes of comparison. The terms "sequence homology" or "homology" in reference to a sequence refers to sequence homology between two amino acid sequence or two nucleotide sequences. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The present invention is based on the discovery that HSF1 activity is mediated by acetylation and deacetylation of amino acids residues within the DNA binding domain. It has been found that acetylation of HSF1 results in decreased binding to DNA whereas maintenance of HSF1 in a deacetylated state prolongs DNA binding. In one embodiment, HSF1 activity in a cell is increased by inhibiting the acetylation of one or more basic amino acids within the DNA binding domain of HSF1. The acetylation of the DNA binding domain of HSF1 can be inhibited by administering an agent that inhibits acetylation of one or more basic amino acid residues within the DNA binding domain. It is to be understood that acetylation of an amino acid is inhibited when acetylation is decreased or deacetylation is increased. In another embodiment, the HSF1 activity is increased by inhibiting the acetylation of a lysine residue within the DNA binding domain of HSF1. In a further embodiment, the HSF1 activity in a cell is increased by inhibiting acetylation of lysine residue 80 of human HSF1 (HSF1 K80) or inhibiting the acetylation of a corresponding conserved amino acid in a non-human HSF1.

The term "HSF1 K80" refers to lysine 80 of human HSF1. A "corresponding conserved amino acid" refers to a lysine residue in the HSF1 of a non-human species that is conserved and corresponds to the human HSF1 K80. As used herein, a "conserved amino acid" or a "conserved residue" refers to an amino acid residue which is found to be in common between two proteins and/or occupies a particular position within a peptide motif, such as in homologous proteins derived from different species. As used herein, a "corresponding conserved amino acid" or a "corresponding conserved residue" in reference to HSF1 K80 refers to the amino acid position for that conserved amino acid in a homologous HSF1 sequence or non-human HSF1 sequence. It will be readily apparent to those skilled in the art that the numbering of amino acids in other homologs of HSF1 can be different from that in human HSF1. Corresponding conserved amino acids in other homologs of HSF1 can be identified by comparison of the amino acid sequences, for example using commercially available homology modeling software packages or conventional sequence alignment packages.

In another embodiment, HSF1 activity in a cell is decreased by promoting the acetylation of one or more basic amino acids within the DNA binding domain of HSF1. In one embodiment, an agent that promotes acetylation of the DNA binding domain is administered to the cell. It is to be understood that the acetylation of an amino acid is promoted when acetylation of the amino acid is increased or when deacetylation is decreased. In another embodiment, the HSF1 activity is decreased by promoting the acetylation of a lysine residue within the DNA binding domain of HSF1. In a further embodiment, the HSF1 activity in a human cell is decreased by promoting the acetylation of human HSF1 K80 or promoting the acetylation of a corresponding conserved amino acid in a non-human HSF1.

As used herein, the term "inhibiting" or "decreasing" encompasses causing a net decrease by either direct or indirect means. The term "increasing" means to cause a net gain by either direct or indirect means.

HSF1 activity refers to the activity of HSF1 as a transcription factor of genes that have the heat shock responsive element (HSE) sequence. Proteins transcribed from genes possessing the HSE sequence are called heat shock (HS) proteins. Heat shock was first discovered as a trigger of the heat shock response leading to enhanced transcription of certain genes [Snoecx et al. (2001), *Physiol. Rev.* 81: 1461-1497]. The products of this transcriptional activity are called heat shock proteins [Snoeckx et al.]. Most heat shock proteins (Hsps) are named with reference to a molecular mass indication, for example, Hsp27. The classification of various Hsps in families is based on their related function and size. The size of heat shock proteins ranges from 10 to 170 kDa. Family names are conventionally written in capitals. For example, "HSP70" refers to the HSP70 family. The HSP70 family range in weight between 70 and 78 kDa. One example of an HSP70 family member is Hsp72 (commonly referred to as Hsp70). The heat shock response encompasses the induction of a gene encoding heat shock proteins. Heat shock protein genes that can be induced according to methods of the present invention include, but are not limited to, a gene encoding a protein from a family selected from the HSP10 family, the HSP40 family, the HSP60 family, the HSP70 family, the HSP90 family, the HSP100 family, the HSP27 family, the αA-crystallin family and the αB-crystallin family of proteins.

Acetylation of HSF1 can be increased by any means (direct or indirect) that results in an increase in the acetylation or a decrease in the deacetylation of HSF1 or that maintains HSF1 in an acetylated form. In some embodiments, acetylation of HSF1 in a cell is increased by administering an agent that increases the acetylation of HSF1. Similarly, acetylation of HSF1 can be decreased or inhibited by any means that results in a decrease in acetylation or an increase in deacetylation or that maintains HSF1 in a deacetylated form. The term "agent" is used herein to denote a chemical compound, a mixture of chemical compounds, a biological macromolecule (including, for example, a nucleic acid, an antibody, a protein or portion thereof, e.g., a peptide), or an extract made from biological materials such as bacteria, plants, fungi, or animal (particularly mammalian) cells or tissues. In one embodiment, an agent that modulates that acetylation of the DNA binding domain of HSF1 can be identified by contacting a cell comprising the HSF1 with a test agent and determining the level of acetylation of the DNA binding domain in the presence and absence of the test compound, wherein an increased in acetylation indicates that the agent increases acetylation of HSF1 and a decrease in acetylation indicates that the agent inhibits acetylated of HSF1.

Exemplary methods of inhibiting the acetylation of HSF1 include, but are not limited to, administering an isolated sirtuin, increasing the activity of a sirtuin in a cell, and inhibiting the activity of histone acetyltransferase (HAT). Histone acetyltransferases (HATs) are enzymes that catalyze the acetylation of lysine residues in specific proteins, including histones, Hsp40/Dna J heat shock proteins and various transcription factors [Saha et al. (2006). HATs and HDACs in neurodegeneration: a tale of disconcerted acetylation homeostasis. Cell Death and Differentiation 13: 539-550; WO 2009/134131 A1]. Several families of acetyltransferases have been identified including the GNAT superfamily (Gen5-related N-acetyltransferases), which includes, for example, prGcn5 and PCAF, the MYST family including, for example, MOZ, Ybf2/Sas3, Sas2 and Tip60, the p300/CBP HAT family including, for example, p300 and CBP proteins (Lau et al. (2000), Cell 5(3): 589-95; U.S. Patent Application Publication No. 20080227752). As shown below in Example 1, p300 and CBP induce HSF1 acetylation.

Histone deacetyltransferases (HDACs) are enzymes that catalyze the deacetylation of lysine residue in their substrates. Deacetylases are grouped into three families; class I and II HDAC families are inhibited by trichostatin A and the NAD+-dependent class III sirtuin family are inhibited by nicotinamide.

In one embodiment, acetylation of HSF1 can be inhibited by administering to the cell an isolated sirtuin or increasing the level or activity of a sirtuin in the cell. The sirtuins are proteins belonging to the sirtuin deacetylase protein family. In one embodiment, the sirtuin belongs to the Sir2 family, which include, but are not limited to, yeast Sir2 (e.g., GenBank Accession No. P53685), *C. elegans* Sir-2.1 (e.g., GenBank Accession No. NP_501912), human SIRT1 (e.g., GenBank Accession No. NM_012238 and NP_036370 (or AF083106)) and human SIRT2 (e.g., GenBank Accession No. NM_012237, NM_030593, NP_036369, NP_085096, and AF083107) proteins. As used herein, the term "Sir2 protein" refers to a sirtuin belonging to the Sir2 family. In one embodiment, the Sir2 protein is SIRT1. In another embodiment, the SIRT1 is human SIRT1.

As described above, one aspect of the invention is a method of increasing the activity of HSF1 in a cell comprising administering to the cell an isolated sirtuin or a biologically active fragment or variant thereof in an amount sufficient to inhibit the acetylation of an amino acid within the DNA binding domain of HSF1.

As used herein, an isolated sirtuin or fragment or variant thereof administered to the cell or to a subject (as described below) is a substantially pure, or substantially pure and isolated polypeptide that has been separated from components that naturally accompany it. It is to be understood that the term "isolated sirtuin" or "isolated SIRT1" does not preclude the inclusion of a pharmaceutically acceptable carrier or excipient and simply indicates that the sirtuin is isolated from the cellular and other components that naturally accompany it. The isolated sirtuin, fragment of variant thereof can be a recombinantly produced polypeptide having the same or substantially identical amino acid sequence as a naturally occurring sirtuin described above.

A biologically active fragment of a sirtuin is a fragment that has deacetylase activity or another biologic activity of a full-length sirtuin. A variant of a sirtuin can be prepared, for example, by making a conservative amino acid substitution in the sequence of sirtuin. A biologically active variant possesses deacetylase activity or another biologic activity of the naturally occurring sirtuin. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (a, v, l, i, p, w, f, and m); another grouping is those amino acids having neutral and polar side chains (g, s, t, y, c, n, and q); another grouping is those amino acids having basic side chains (k, r, and h); another grouping is those amino acids having acidic side chains (d and e); another grouping is those amino acids having aliphatic side chains (g, a, v, l, and i); another grouping is those amino acids having aliphatic-hydroxyl side chains (s and t); another grouping is those amino acids having amine-containing side chains (m, q, k, r, and h); another grouping is those amino acids having aromatic side chains (f, y, and w); and another grouping is those amino acids having sulfur-containing side chains (c and m). Exemplary conservative amino acid substitutions groups are: r-k; e-d, y-f, l-m; v-i, and q-h. The amino acids are described above using their commonly assigned one-letter designations: a for alanine; c for cysteine; d for aspartic acid; e for glutamic acid; f for phenylalanine; g for glycine; h for histidine; i for isoleucine; k for lysine; l for leucine; m for methionine; n for asparagines; p for proline; q for glutamine; r for arginine; s for serine; t for threonine; v for valine; w for tryptophan; and y for tyrosine.

In one embodiment, the sirtuin is a Sir2 protein or a biologically active fragment or variant thereof. In another embodiment, the sirtuin is peptide having at least about 80%, 85%, 90%, 95%, 98% and 99% sequence homology to a naturally occurring Sir2 protein or a fragment thereof. In another embodiment, the sirtuin is a peptide having at least about 80%, 85%, 90%, 95%, 98% and 99% sequence identity to a naturally occurring Sir2 protein or a fragment thereof. In another embodiment, the Sir2 protein is a peptide having at least about 80%, 85%, 90%, 95%, 98% and 99% sequence identity to a mammalian SIRT1. In another embodiment, the Sir2 protein is a peptide having at least about 80%, 85%, 90%, 95%, 98% and 99% sequence identity to a human SIRT1. In a further embodiment, the Sir2 protein is a peptide having at least 80%, 85%, 90%, 95%, 98% and 99% sequence identity to SEQ ID NO:2.

In another embodiment, the Sir2 protein has at least about 80% sequence identity to the 250 amino acid conserved SIRT1 catalytic domain, amino acid residues 258 to 451 of SEQ ID NO: 2. SEQ ID NO:2 shows the amino acid sequence of human SIRT1. In preferred embodiments, the Sir2 protein comprises a sequence that has at least about 80, 85, 90, 95, 99% sequence identity to the amino acid sequence between amino acid residues 258 and 451 of SEQ ID NO:2. In other embodiments, the Sir2 protein is a biologically active fragment of a full length Sir2 protein, e.g., a fragment of SIRT1 capable of deacetylation. Sir2 proteins also include sequences or variants that include one or more substitutions, e.g., between one and ten substitutions, with respect to a naturally occurring Sir2 family member.

The level or activity of a sirtuin can also be increased by administering an agent that increases the level or activity of the sirtuin in the cell ("sirtuin activating agent"). The activity of a sirtuin refers to deacetylase activity or the ability of the protein to deacetylate a substrate or to another biologic activity of a sirtuin.

A sirtuin activating agent is an agent that increases the activity of a sirtuin. A SIRT1 activating agent is an agent that increases the activity of a SIRT1 in a cell. Sirtuin and SIRT1 activating compounds have been described, for example, in U.S. Pat. No. 7,345,178, U.S. Patent Application Publication No.'s. 20080249103, 20080194803, 200070037865, 20070014833, 20060229265 and 20060025337 and International Application No.'s. WO 2005/002672, WO 2005/002555, WO 2009015180, WO 2009015179, WO 2006094248, WO 2006004722, WO 2006094235, WO 2006094233, WO 2006094209, WO 2006105440, WO 2006078941, WO 2006094236, WO 2006/094210 and also in Milne et al. (2007), *Nature* 450: 712-716, and Szczepankiewicz et al. (2008), *Current Topics in Medical Chemistry* 8: 1533-1544, the contents of each of which herein incorporated by references. Specific SIRT1 activating compounds include, but are not limited to, flavones, stilbenes, flavanones, isoflavanones, catechins, chalcones, tannins and anthocyadins, quinoxalines (e.g., pyrroloquinoxalines), SRT-1460, SRT-2183, SRT-1720, SRT-2104, oxaloacetates, resveratrol, oxazolo[4,5-b]pyridine, azabenzimidazoles, benzimidazoles, and imidazothiazoles (e.g., SRT1460, SRT2183 and SRT1720), (Szczepankiewicz et al.). Exemplary stilbenes include, but are not limited to, hydroxystilbenes, such as trihydroxystilbenes, e.g., 3,5,4'-trihydroxystilbene ("resveratrol"). Resveratrol is also known as 3,4',5-stilbenetriol. Certain resveratrol ester analogues have also been described as sirtuin activators (see, for example, WO 2005069998). Tetrahydroxy-stilbenes, e.g., piceatannol, are also encompassed. Hydroxychalones including trihydroxychalones, such as isoliquiritigenin, and tetrahydroxychalones, such as butein, have also been described as SIRT1 activating compounds. Hydroxyflavones including tetrahydroxyflavones, such as fisetin, and pentahydroxyflavones, such as quercetin, can also be used. Exemplary hydroxyflavone that are SIRT1 activators include, but are not limited to isoquiritigenin, fisetin, butein, and quercetin.

In another embodiment, acetylation of HSF1 can be inhibited by administering to the cell an agent that inhibits the activity of a histone acetyltransferase (HAT) or an inhibitor of histone acetyltransferase (HAT). Exemplary HAT inhibitors include anacardic acid (6-pentadecylsalicylic acid) and derivatives thereof described, for example, in U.S. Patent Application Publication No. 20090076155, the contents of which are expressly incorporated by reference herein. Curcumanoids (including, for example, curcumin), epigallogatechin-3-gallate and garcinol have also been described as HAT inhibitors (see, for example, U.S. Patent Application Publication No. 20060020027, Cancer Research 69, 583 (2009), and JBC 279: 33716-33726, respectively, the contents of each of which are expressly incorporated by reference herein). Other compounds and method for inhibiting HAT have been described in U.S. Patent Application Publication No. 20090076155, WO 02070675, US Patent Application Publication No. 2008227752 and U.S. Pat. Nos. 6,369,030 and 6,747,005, the contents of each of which are expressly incorporated by reference herein. p300 inhibitors have been described, for example, in U.S. Patent Application Publication No. 20050069986 and Lau et al. (2000), Cell 5(3): 589-95, Mai et al. (2009), Bioorganic and Medicinal Chemical Letters 19(4): 1132-35, the contents of each of which are expressly incorporated by reference.

The invention is also directed to a method of decreasing the activity of HSF1 in a cell by promoting the acetylation of the DNA binding domain of HSF1 comprising decreasing the activity of a sirtuin. In one embodiment, the sirtuin is a Sir2 protein. In another embodiment, the sirtuin is SIRT1. In one embodiment, an agent that inhibits the activity of a sirtuin ("sirtuin inhibiting agent") can be administered to the cell. In one embodiment, a SIRT1 inhibiting agent is administered.

As will be appreciated by the skilled artisan, a sirtuin inhibiting agent can be a small molecule, a protein, a peptide, a peptidomimetic, an antibody or a nucleic acid. Nucleic acids include, but are not limited to, DNA, RNA, an RNA interfering agent and PNA. Sirtuin inhibiting agents have been described in U.S. Pat. No. 7,345,178, U.S. Patent Application Publication No.'s. 20080287653, 20060229265, 20060084135, 20050136537 and 20070197459, International Application No.'s. WO 2008155390, WO 2008011476, WO 2008082646, WO 2008156866, WO 2008086400, WO 2007047604, WO 2007084162, WO 2006099245, WO 2006094209, WO 2006/094210, WO 2005026112, and WO 2005060711, the contents of each of which are herein incorporated by reference. Exemplary small molecule sirtuin inhibiting agents are nicotinamide, sirtinol, para-sirtinol, HR-73, 2,3,4,9-tetrahydro-1H-carbazole-1-carboxyamide, splitomicin, SEN-196, 2-phenylaminobenzamide, suramin, NSC-112546, cambinol, tenovin-1, guttiferone, hyperforin, artisoforin and the protein kinase C inhibitors Ro31-8220, rottlerin, ZM449829 and indirubin-3'-monooxime (Szczepankiewicz et al.).

In another embodiment, the sirtuin inhibiting agent is anti-sirtuin antibody. The term antibody encompasses monoclonal antibodies, polyclonal antibodies, humanized antibodies, chimeric antibodies, single-chain Fv (scFv), Fab fragment, F(ab') fragments, intrabodies, and synthetic antibodies. In one embodiment, the sirtuin inhibiting agent is an anti-Sir2 protein antibody. In a further embodiment, the sirtuin inhibiting agent is an anti-SIRT1 antibody. Anti-sirtuin antibodies can be raised against an appropriate immunogen, including sirtuin proteins or polypeptides or fragments thereof (including synthetic molecules, such as synthetic peptides). Preparation of immunizing antigen, and polyclonal and monoclonal antibody production can be performed using any suitable technique, including, for example, a phage display. A variety of methods have been described (see e.g., Kohler et al., *Nature*, 256:495-497 (1975)) and *Eur. J. Immunol.* 6:511-519 (1976)); Milstein et al., *Nature* 266:550-552 (1977)); U.S. Pat. No. 4,172,124; Harlow, E. and D. Lane, 1988, *Antibodies: A Laboratory Manual*, (Cold Spring Harbor Laboratory: Cold Spring Harbor, N.Y.); and *Current Protocols In Molecular Biology*, Vol. 2 (Supplement 27, Summer '94), Ausubel, F. M. et al., Eds., (John Wiley & Sons: New York, N.Y.), Chapter 11, 1991); the teachings of each of which are incorporated herein by reference). Fragments of antibodies can also be used according to the present invention. Antibodies can be fragmented using conventional techniques and the fragments screened for utility in the same manner as whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab fragments can be prepared by proteolytic digestion of substantially intact immunoglobulin molecules with papain using methods that are well known in the art. However, a Fab fragment may also be prepared by expressing in a suitable host cell the desired portions of immunoglobulin heavy chain and immunoglobulin light chain using any methods known in the art. The anti-sirtuin antibody can also be an intrabody. An intrabody is an intracellularly expressed antibody, a single-chain antibody molecule designed to specifically bind and inactivate target molecules inside cells. Intrabodies have been used in cell assays and in whole organisms [Chen et al., *Hum. Gen. Ther.* (1994) 5:595-601; Hassanzadeh et al., *Febs Lett.* (1998) 16(1, 2):75-80 and 81-86]. Inducible expression vectors can be constructed with intrabodies that react specifically with a sirtuin.

In a further embodiment, the sirtuin inhibiting agent is a nucleic acid. In one embodiment, the nucleic acid is an antisense nucleic acid. The antisense nucleic acid can be RNA, DNA, a PNA or any other appropriate nucleic acid molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, for example, for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, for example, in U.S. Pat. Nos. 6,242,258, 6,500, 615, 6,498,035, 6,395,544 and 5,563,050, the contents of each of which are herein incorporated by reference.

In another embodiment, the sirtuin inhibiting agent is an RNA interfering agent. An "RNA interfering agent" as used herein, is defined as any agent that interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi). The target gene of the present invention is a gene encoding a sirtuin. In one embodiment, the gene encodes a Sir2 protein. In another embodiment, the gene encodes SIRT1. In yet another embodiment, the gene encodes human SIRT1. As used herein, "inhibition of target gene expression" includes any decrease in expression or protein activity or level of the target gene or protein encoded by the target gene.

In one embodiment, the RNA interfering agent is an siRNA. The siRNA can be chemically synthesized, can be produced by in vitro transcription, or can be produced within a host cell. In one embodiment, siRNA is a double stranded RNA (dsRNA) molecule of about 15 to about 40 nucleotides in length or about 15 to about 28 nucleotides or about 19 to about 25 nucleotides in length or about 19, 20, 21, or 22 nucleotides in length, and may contain a 3' and/or 5' overhang on each strand having a length of about 0, 1, 2, 3, 4, 5, or 6 nucleotides. The length of the overhang is independent between the two strands, i.e., the length of the overhang on one strand is not dependent on the length of the overhang on the second strand.

RNAi also includes small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand may follow. These shRNAs can be contained in plasmids, retroviruses, and lentiviruses and expressed from, for example, the pol III U6 promoter, or another promoter (see, e.g., Stewart, et al. (2003) *RNA* April; 9(4):493-501, incorporated by reference herein).

In addition to RNA, RNA interfering agents can also be comprised of chemically modified nucleotides and non-nucleotides, and also include molecules wherein a ribose sugar molecule is substituted for another sugar molecule or a molecule which performs a similar function. In addition, a non-natural linkage between nucleotide residues may be used, such as a phosphorothioate linkage. The RNA strand can be derivatized with a reactive functional group of a reporter group, such as a fluorophore. Exemplary derivatives are modified at a terminus or termini of an RNA strand, typically the 3' terminus of the sense strand. Other exemplary derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified, for example, they can be alkylated or halogenated. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can additionally be incorporated.

In another embodiment, the nucleic acid is a ribozyme or a deoxyribozyme. Ribozymes and deoxyribozymes have been shown to catalyze the sequence-specific cleavage of nucleic acid molecules. The cleavage site is determined by complementary pairing of nucleotides in the RNA or DNA enzyme with nucleotides in the target nucleic acid. Thus, RNA and DNA enzymes can be designed to cleave to a nucleic acid molecule, thereby increasing its rate of degradation [Cotten et al, *EMBO J.* 8: 3861-3866, 1989; Usman et al., *Nucl. Acids Mol. Biol.* 10: 243, 1996; Usman, et al., *Curr. Opin. Struct. Biol.* 1: 527, 1996; Sun, et al., *Pharmacol. Rev.,* 52: 325, 2000].

Sirtuin inhibiting compounds also encompass peptide aptamers. Peptide aptamers are peptides or small polypeptides that act as dominant inhibitors of protein function. Peptide aptamers bind specifically to target proteins, blocking their function (Kolonin and Finley, *PNAS* (1998) 95:14266-14271). Peptide aptamers that bind with high affinity and specificity to a sirtuin can be isolated by a variety of techniques known in the art. Peptide aptamers can be isolated from random peptide libraries by yeast two-hybrid screens (Xu et al., *PNAS* (1997) 94:12473-12478). They can also be isolated from phage libraries (Hoogenboom et al., *Immunotechnology* (1998) 4:1-20) or chemically generated peptides/libraries.

In certain aspects, the activity of HSF1 can be inhibited by administering an agent capable of increasing the activity of a HAT (also referred to herein as a HAT activator). An example of small molecule compound capable of activating HAT is N-(4-chloro-3-trifluoromethyl-phenyl)-2-ethoxy-6-pentadecyl-benzamide (CTPB) (Balasubrmanyam et al. (2003). Small molecule modulators of histone acetyltransferase p300. The Journal of Biological Chemistry, 278, 19134-19140).

According to the inventive methods, the activity of HSF1 can be modulated in a cell by modifying the acetylation of a basic amino acid residue within the DNA binding domain of the HSF1. Cells include prokaryotic cell, eukaryotic cells, vertebrate cells and invertebrate cells. In one embodiment, the cell is a mammalian cell. In another embodiment, the cell is a human cell. Exemplary cells include, but are not limited to, muscle cells (e.g., skeletal muscle cells, and cardiac muscle cells such as pacemaker cells, atrial cells, atrial-ventricular nodal cells, left ventricular cells, right ventricular cells, papillary muscle cells, and Purkinje fiber cells and smooth muscle cells), blood cells, kidney cells, epithelial cells, intestinal cells, lymph node cells, spleen cells, hepatic cells, thymic cells, salivary gland cells, pituitary cells, bladder cells, bone cells, breast cells, cervical cells, colorectal cells, kidney cells, laryngeal cells, pulmonary cells, lymphatic cells, skin cells and haematopoietic cells (such as for instance T lymphocytes, B lymphocytes, macrophages, dendritic cells and progenitors thereof).

In certain aspects, the invention is a method of modulating the activity of HSF1 in a subject in need thereof comprising administering to said subject an effective amount of an agent that modifies acetylation of a basic amino acid residue within the DNA binding domain of HSF1. In one embodiment, the invention is a method of increasing the activity of HSF1 in a subject in need thereof comprising administering to said subject an effective amount of an agent that inhibits the acetylation of a basic amino acid residue with the DNA binding domain of HSF1. In a further embodiment, the agent that inhibits the acetylation of the DNA binding domain of HSF1 is an isolated sirtuin, a sirtuin activating agent or a HAT inhibitor. In another embodiment, the invention is a method of decreasing the activity of HSF1 in a subject in need thereof comprising administering to said subject an effective amount of an agent that promotes acetylation of a basic amino acid residue within the DNA binding domain of HSF1. In a further embodiment, the agent that promotes acetylation of the DNA binding domain of HSF1 is a sirtuin inhibiting agent or a HAT activator.

The invention also encompasses a method of treating a condition associated with a dysfunction in protein homeostasis in a patient in need thereof comprising administering to said patient a therapeutically effective amount of an agent that inhibits acetylation of a basic residue in the DNA binding domain of HSF1. In another embodiment, the agent inhibits acetylation of a lysine residue within the DNA binding domain. In a further embodiment, the agent inhibits acetylation of HSF1 K80. In yet another embodiment, the method comprises administering to said patient a therapeutically effective amount of an agent selected from the group consisting of a HAT inhibitor, an isolated sirtuin and a sirtuin activating agent. In one embodiment, the agent is a HAT inhibitor. In another embodiment, the agent is an isolated sirtuin. In another embodiment, the sirtuin is a Sir2 protein. In a further embodiment, the sirtuin is a SIRT1. In an additional embodiment, the sirtuin is human SIRT1. In yet another embodiment, the agent is a sirtuin activating agent or SIRT1 activating agent. Sirtuin activating agents have been defined and described above. As described above, sirtuin activating agents and SIRT1 activating agents include, for example, flavones, stillbenes, flavanones, isoflavanones, catechins, chalcones, tannins and anthocyadins, pyrroloquinoxaline, SRT-1460, SRT-2183, SRT-1720, oxaloacetates, resveratrol and other polyphenols. The isolated sirtuins or sirtuin activating agents can be administered in a pharmaceutical composition comprising a pharmaceutically carrier or excipient.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment. A "therapeutically effective amount" refers to that amount of the therapeutic agent that sufficient to amelioration of one or more symptoms of a disorder and/or prevent advancement of a disorder, cause regression of the disorder.

The invention encompasses the treatment of a condition associated with a dysfunction in the homeostasis of a protein. Exemplary proteins include glucocerebrosidase, hexosamine A, cystic fibrosis transmembrane conductance regulator, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α1 anti-trypsin, α-N-acetylgalactosaminidase, α-neuramidase, β-glucuronidase, β-hexosamine A and acid lipase, polyglutamine, α-synuclein, Ab peptide, tau protein, hERG potassium channel, islet amyloid polypeptide, and transthyretin.

In one embodiment, the disease associated with a dysfunction in proteostasis is a gain of function disorder. The terms "gain of function disorder," "gain of function disease," "gain of toxic function disorder" and "gain of toxic function disease" are used interchangeably. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease, type II diabetes, liver disease and prion diseases. Neurodegenerative diseases associated with aggregation of polyglutamine include, but are not limited to, Huntington's disease, dentatorubral and pallidoluysian atrophy, several forms of spinocerebellar ataxia, and spinal and bulbar muscular atrophy Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru.

In a further embodiment, the disease associated with a dysfunction in protein homeostasis is a loss of function disorder. The terms "loss of function disease" and "loss of function disorder" are used interchangeably. Loss of function diseases are a group of diseases characterized by inefficient folding of a protein resulting in excessive degradation of the protein. Loss of function diseases include, for example, cystic fibrosis, emphysema, and lysosomal storage diseases. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gml gangliosidosis, Hunter's disease, Hurler-Scheie's disease, Krabbe's disease, a-Mannosidosis, B-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, the disease associated with a dysfunction in proteostasis and/or heat shock proteins is a cardiovascular disease. Cardiovascular diseases include, but are not limited to coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

The invention also encompasses a method of treating a patient suffering from a condition associated with a dysfunction in proteostasis comprising administering a therapeutically effective amount of an agent that inhibits acetylation of a lysine residue in the DNA binding domain of HSF1 in combination with administration of a pharmacologic chaperone. Pharmacologic chaperones or kinetic stabilizers refer to compounds that bind an existing steady state level of the folded mutant protein and chemically enhance the folding equilibrium by stabilizing the fold [Bouvier, *Chem Biol* 14: 241-242, 2007; Fan et al., *Nat Med* 5: 112-115, 1999; Sawkar et al., *Proc Natl Acad Sci USA* 99:15428-15433, 2002; Johnson and Kelly, *Accounts of Chemical Research* 38: 911-921, 2005]. The pharmacologic chaperone is administered in amount that in combination with a sirtuin activating compound is sufficient to treat a patient suffering from a condition associated with a dysfunction in proteostasis. Exemplary pharmacologic chaperones are described in U.S. Patent Publication No.'s. 20080056994, 20080009516, 20070281975, 20050130972, 20050137223, 20050203019, 20060264467 and 20060287358, the contents of which are incorporated by reference herein.

In another embodiment, the invention is a method of treating a patient suffering from a condition associated with a dysfunction in proteostasis an agent that inhibits acetylation of a lysine residue in the DNA binding domain of HSF1 in combination with the administration of a mechanistically distinct proteostasis regulator. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the HSR signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. A mechanistically distinct proteostasis regulator is a proteostasis regulator that enhances cellular proteostasis by a mechanism other than by modulating acetylation of HSF1. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., J Biol Chem, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol.

In certain aspects, the invention is a method of treating a patient suffering from a condition associated with a dysfunction in proteostasis comprising administering an agent that inhibits acetylation of a lysine residue in the DNA binding domain of HSF1 in combination with the administration of a mechanistically distinct proteostasis regulator, wherein the proteostasis regulator is a heat shock response activator. A heat shock response activator is an agent that indirectly or directly activates or increases the heat shock response, for example, by directly or indirectly activating heat shock transcription factor 1 (HSF1), increasing Hsp70 transcription or protein expression, inhibiting Hsp90, and/or activating or increasing chaperone mRNA or protein expression (Westerheide et al., J Biol Chem, 2004. 279(53): pp. 56053-60, the contents of which are expressly incorporated by reference herein). It is to be understood that heat shock response activators encompass agents that indirectly or directly increase a basal heat shock response. The terms "heat shock response activator," "heat shock activator," "heat shock response inducer," and "heat shock inducer" are used interchangeably herein. Non-limiting examples of heat shock response activators are celastrols, non-steroidal anti-inflammatory drugs, ansamycin, geldenamycin, radiciol, glucuronic acid, and tributylin. Heat shock response activators have also been described, for example, in U.S. Patent Application Publication No.'s. 20070259820, 20070207992, 20070179087, 20060148767, the contents of each of which are expressly incorporated by reference herein. In some embodiments, the heat shock response activator is a small molecule heat shock response activator. The agent that inhibits acetylation of a lysine residue in the DNA binding domain of HSF1 and the heat shock response activator can each be administered at a dose wherein the combined doses of the heat shock response activator and agent that inhibits acetylation are together sufficient to increase a heat shock response. Combining heat shock activator and the agent that inhibits acetylation of HSF1 results in a greater increase in heat shock response than when either of the agents is administered alone. In some embodiments, although the dose of heat shock activator administered may not alone be sufficient to induce a heat shock response, the dose is sufficient to activate a heat shock response in combination with the agent that inhibits acetylation of a lysine residue in the DNA binding domain of HSF1. In some aspects of the invention, the combination of heat shock activator and the agent that inhibits acetylation of the DNA binding domain of HSF1 has a greater than an additive effect on the induction of the heat shock response. In other aspects, the increase in heat shock response is determined by measuring an increase in Hsp70 transcription or protein expression. An exemplary method of measuring the increase in heat shock response is described in Westerheide et al. (2004). *Celastrols as inducers of the heat shock response and cytoprotection.* J Biol Chem, 2004. 279(53): pp. 56053-60, the contents of which are incorporated by reference herein. In additional aspects, the increase in heat shock response after administration of the combination of heat shock response activator and agent that inhibits acetylation of HSF1 encompasses an increase in Hsp70 transcription or protein expression that is at least about 2-fold, at least about 3-fold, at least about 5-fold, at least about 10-fold, at least about 15-fold, or at least about 20-fold greater than the heat shock response in the absence of the combination of agents.

As shown in Example 2, it has been found that a lower dose of a heat shock activator can be administered to induce a heat shock response when an agent that inhibits acetylation of a lysine residue in the DNA binding domain of HSF1 is also administered. Lowering the dose or EC50 of a heat shock response activator can be advantageous because there are circumstances in which the dose of heat shock response activator required for inducing the heat shock response also results in toxicity. Therefore, in some embodiments, the invention is directed to a method of activating or increasing a heat shock response comprising administering a heat shock response activator in combination with an agent that inhibits acetylation of a lysine residue in the DNA binding domain of HSF1, wherein the combined doses of the heat shock response activator and agent that inhibits acetylation of a lysine residue in the DNA binding domain of HSF1 are together sufficient to activate or increase a heat shock response. In other embodiments, the invention is a method of lowering the dose of a heat shock response activator effective for inducing a heat shock response in patient in need thereof, comprising administering an agent that inhibits acetylation of a lysine residue in the DNA binding domain of HSF1 and heat shock response activator. It is to be understood that an agent that inhibits acetylation of a lysine residue in the DNA binding domain of HSF1 can be administered in combination with another agent when both agents are part of the same composition and/or when both agents are administered at the same time and/or when both agents are administered at different times or sequentially. In one embodiment, the agent that inhibits acetylation of a lysine residue in the DNA binding domain of HSF1 is administered before the heat shock response activator.

In certain other embodiments, the invention is directed to a pharmaceutical composition comprising a heat shock response activator and an agent that inhibits the acetylation of HSF1. In other embodiments, the pharmaceutical composition comprises a heat shock activator and an agent that inhibits the acetylation of HSF1 selected from the group consisting of a HAT inhibitor, an isolated sirtuin and a sirtuin activating agent. In other embodiments, the invention is a pharmaceutical composition comprising a heat shock response activator and a SIRT1 activating agent. In an additional embodiment, the invention is a pharmaceutical composition comprising a heat shock response activator and a HAT inhibitor.

In another aspect, the invention is a method of treating a condition associated with increased expression of heat shock proteins in a patient in need thereof comprising administering to said patient a therapeutically effective amount of an agent that promotes acetylation of the DNA binding domain of HSF1. In one embodiment, the agent that promotes acetylation of HSF1 is a sirtuin inhibiting agent. In another embodiment, the agent that promotes acetylation of HSF1 is HAT activator. Sirtuin inhibiting agents have been described above. In another embodiment, the condition associated with increased expression of a heat shock protein is cancer or a tumor. In yet another embodiment, the condition associated with increased expression of a heat shock protein is a viral infection. The agent that promotes acetylation of HSF1 can be administered in a pharmaceutical composition comprising a pharmaceutically carrier or excipient.

The condition associated with increased expression of heat shock proteins can be cancer or a tumor. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering an agent that promotes acetylation of HSF1 in combination with the administration of a chemotherapeutic agent. Chemotherapeutic agents that can be utilized include, but are not limited to, alkylating agents such as cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising promoting acetylation of HSF1 in combination with radiation therapy.

In another embodiment, the condition associated with increased expression of a heat shock protein is a viral infection. In a further embodiment, the viral infection is caused by a virus selected from a tumor virus and an RNA virus. Exemplary tumor viruses are the herpes viruses, the papiloma viruses, the polyoma viruses and HTLV-1 [McCance et al. *Human Tumor Viruses*, 1998, American Society for Microbiology]. Herpes viruses include, but are not limited to, EBV (HHV-4), HHV-6 and HHV-8. Papilomaviruses include, but are not limited to, HPV-1, -2, -4, -5, -6, -8, -6, -11, -16, -18, -31, -33, -35, -45, -51, -52, -58 and -58.

RNA viruses include, for example, arenaviridae, bunyaviridae, calciviridae, coronaviridae, filoviridae, flaviridae, orthomyxoviridae, Paramyxoviridae, picornaviridae, reoviridae, rhabdoviridae, retroviridae, or togaviridae. Exemplary RNA viruses include, but are not limited to, the human coronaviruses, such as the SARS-Associated Coronavirus, human toroviruses associated with enteric and respiratory diseases; the Norwalk virus. Yellow Fever virus, West Nile virus, Hepatitis C virus, Dengue fever virus, Polio virus, the common cold virus, hepatitis A virus, hepatitis E, rotavirus, Borna disease virus; Bunyaviradae, such as Hanta virus, California encephalitis virus, Japanese encephalitis virus, LaCrosse virus, Rift Valley fever virus, Bunyavirus, Arbovirus, Ebola virus and Marburg virus; Influenza virus type A, Influenza virus type B, Influenza virus type C, Mumps virus, Measles virus, Subacute sclerosing panencephalitis (SSPE) virus and Respiratory syncytial virus (RSV).

In a further embodiment the invention is a method of treating a patient suffering from a viral infection comprising administering an agent that promotes acetylation of HSF1 in combination with the administration of an anti-viral drug.

In yet another aspect of the invention, the condition associated with increased expression of a heat shock protein is an inflammatory condition and/or an autoimmune disease.

The form of a pharmacologic agent or pharmaceutical composition used according to the inventive methods of treatment depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

For parenteral administration, pharmaceutical compositions or pharmacologic agents can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The compositions can be prepared as injectable formulations, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., Eur. J. Immunol. 25: 3521-24, 1995; Cevc et al., *Biochem. Biophys. Acta* 1368: 201-15, 1998].

In another embodiment, the invention is a method of identifying an agent that modulates HSF1 activity in a cell comprising:
administering a test agent to a cell; and
monitoring the acetylation of lysine residues within the DNA binding domain of the HSF1;

wherein a change in the acetylation of the DNA binding domain relative to that in the absence of the test agent indicates that the test agent modulates HSF1 activity in the cell.

Test agents can be obtained from a wide variety of sources including libraries of synthetic or natural compounds. For example, numerous means are available for random and directed synthesis of a wide variety of organic compounds and other agents. Libraries of natural compounds in the form of bacterial, fungal, plant and animal extracts are also available or can be readily produced. Additionally, natural or synthetically produced libraries and compounds are readily modified through conventional chemical, physical and biochemical means, and can be used to produce combinatorial libraries. Pharmacologic agents can also be subjected to directed or random chemical modifications, such as acylation, alkylation, esterification, amidification, etc. to produce structural analogs. Test agents encompass numerous chemical classes, typically synthetic, semi-synthetic, or naturally-occurring inorganic or organic molecules. Test agents include those found in large libraries of synthetic or natural compounds.

In one embodiment, the test agent inhibits the acetylation of the DNA binding domain. In another embodiment, the test agent increases the acetylation of the DNA binding domain. In a further embodiment, the acetylation of a lysine in the DNA binding domain is monitored. For example, HSF1 K80 or a corresponding conserved amino acid in a non-human HSF1 can be monitored. In an additional embodiment, the cell is a human cell.

In yet another embodiment, the invention is a method of identifying an agent that modulates HSF1 activity comprising:
a. Administering a test agent to a cell or cell lysate;
b. Measuring the acetylation of a sirtuin substrate;
c. Comparing the acetylation of the sirtuin substrate in step (b) to the acetylation of the sirtuin substrate in the absence of the test agent;
wherein increased acetylation of the sirtuin substrate after administration of the test agent indicates that the test agent inhibits HSF1 activity and wherein decreased acetylation of the sirtuin substrate after administration of the test agent indicates that the test agent increases HSF1 activity. A sirtuin substrate is an agent (such as a protein or peptide) that is capable of being deacetylated by the sirtuin. In one embodiment, the sirtuin substrate is HSF1. In another embodiment, the sirtuin substrate is a substrate other than HSF1. The acetylation of the sirtuin substrate can be measured, for example, in a cell homogenate. In one embodiment, the test agent inhibits sirtuin activity. In another embodiment, the test agent activates sirtuin activity. In a further embodiment, the sirtuin is SIRT1. In yet another embodiment, the sirtuin is a human SIRT1. In another embodiment, the cell is a human cell. Assays for measuring sirtuin deacetylase activity and for measuring acetylation of sirtuin substrates have been described, for example in U.S. Patent Application Publication No. 20080249103, the contents of which are incorporated by reference herein.

In yet another embodiment, the invention is a method of identifying an agent that modulates HSF1 activity comprising:
a. Administering a test agent to a cell or cell lysate;
b. Measuring the acetylation of a HAT substrate;
c. Comparing the acetylation of the HAT substrate in step (b) to the acetylation of the HAT substrate in the absence of the test agent;
wherein increased acetylation of the HAT substrate after administration of the test agent indicates that the test agent inhibits HSF1 activity and wherein decreased acetylation of the HAT substrate after administration of the test agent indicates that the test agent increases HSF1 activity. A HAT substrate is an agent (such as a protein or peptide) that is capable of being acetylated by the histone acetyltransferase. In some aspects, the HAT substrate is not HSF1.

In another aspect, the invention is an agent that modulates HSF1 activity identified by a method described herein.

The invention is illustrated by the following examples which are not meant to be limiting in any way.

EXEMPLIFICATION

Example 1

Stress-Inducible Regulation of Heat Shock Factor 1 by the Deacetylase SIRT1

Heat shock factor 1 (HSF1) is essential for protecting cells from protein-damaging stress associated with misfolded proteins and regulates the insulin-signaling pathway and aging. Here, we show that human HSF1 is inducibly acetylated at a critical residue that negatively regulates DNA binding activity. Activation of the deacetylase and longevity factor SIRT1 prolonged HSF1 binding to the Hsp70 promoter by maintaining HSF1 in a deacetylated, DNA-binding competent state. Conversely, downregulation of SIRT1 accelerated the attenuation of the heat shock response (HSR) and release of HSF1 from its cognate promoter elements. These results provide a mechanistic basis for the requirement of HSF1 in the regulation of lifespan and establish a role for SIRT1 in protein homeostasis and the HSR.

Transient activation of HSF1 by diverse environmental and physiological stress is a multi-step process that involves constitutive expression of an inert HSF1 monomer, conversion of the monomer to a DNA-binding competent trimer, increased phosphorylation of HSF1 at serine residues, enhanced transcription, and attenuation of HSF1 DNA-binding and transcriptional activity (1). HSF1 activates the transcription of a large number of genes that regulate protein homeostasis including the molecular chaperones Hsp70 and Hsp90. These chaperones associate with HSF1 to initiate a negative feedback loop and inhibit HSF1 transcriptional activity (2). However, HSF1 is not released from its target promoter sites (3), suggesting that additional mechanisms must exist to complete the HSF1 cycle.

Stress resistance and metabolic state are intimately coupled to protein homeostasis and increased lifespan. In *C. elegans*, the protective effects of reduced insulin signaling require HSF1 and the FOXO transcription factor DAF-16 to prevent protein misfolding damage and promote longevity (4, 5). The beneficial effects of low caloric intake are mediated by the sirtuin family member Sir2, an NAD-dependent deacetylase that is under metabolic control (6). The mammalian Sir2 homolog SIRT1 regulates the transcription factor FOXO3 among other cellular protective pathways (7). We therefore tested whether the sirtuins, specifically SIRT1, regulate HSF1 activity and thereby provide a direct link between these three longevity factors.

We treated HeLa cells with the sirtuin inhibitor nicotinamide (8), and then exposed the cells to various stresses known to induce the HSR (9). Nicotinamide treatment decreased abundance of the stress-induced mRNAs from all major classes of heat shock genes (hsp70, hsp90, hsp40 and hsp27, FIG. 1A), indicating that the sirtuins are required for full induction of the HSR. Of three nuclear sirtuins, SIRT1 has well characterized targets (10). We therefore investigated SIRT1 as a candidate for regulation of the HSR. Upon depletion of SIRT1 by siRNA, the amount of hsp70 mRNA produced during a 6-hour heat shock (HS) was one fourth of that in cells transfected with control siRNA (FIG. 1B).

Figure 1:
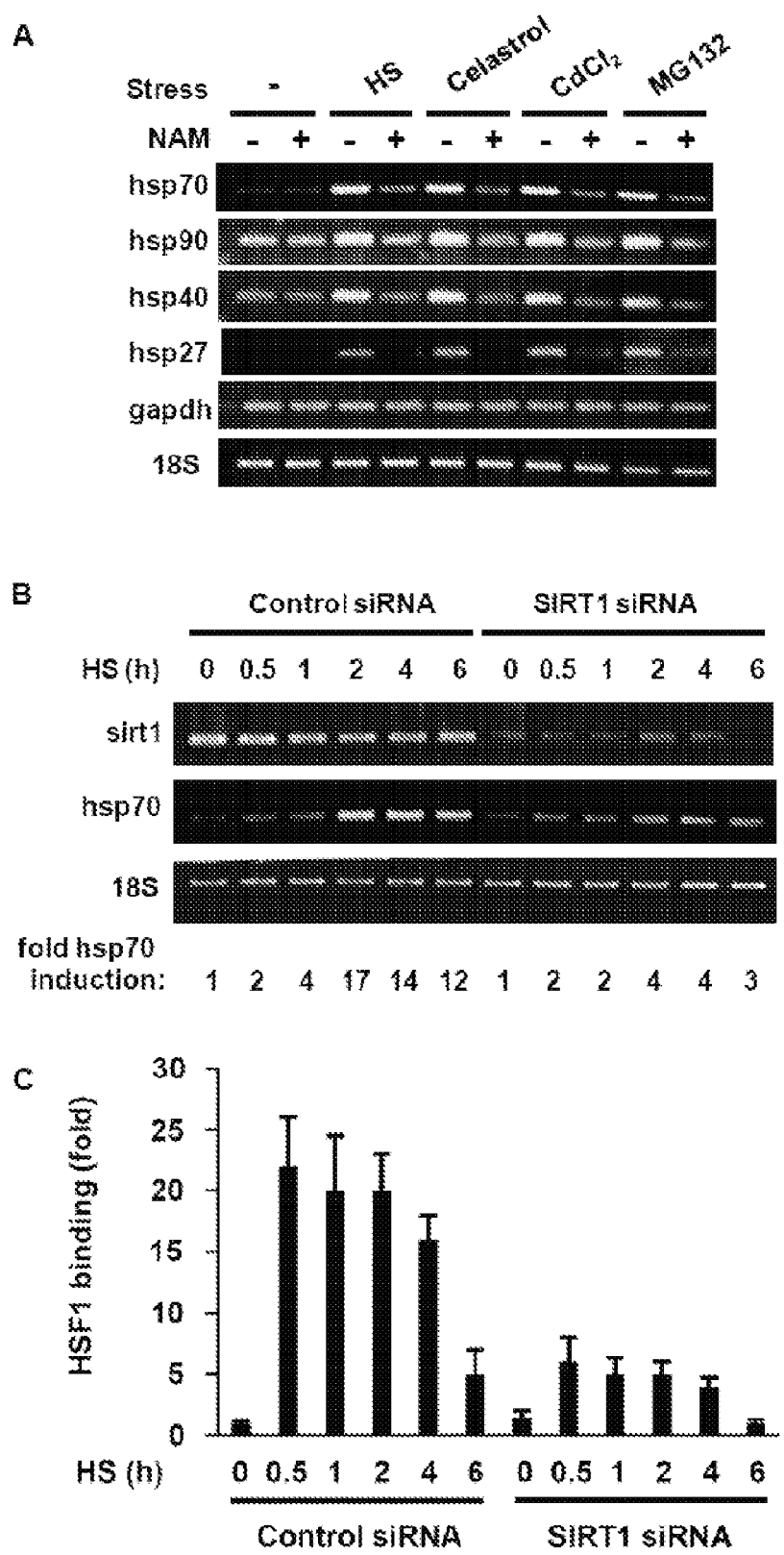
FIG. 1A: Effect of sirtuin inhibitor nicotinamide on chaperone gene expression. HeLa cells were treated with nicotinamide (NAM) prior to exposure to heat shock (HS), celastrol, $CdCl_2$, or MG132 and RT-PCR analysis was performed with the indicated primers.
FIG. 1B: SIRT1 siRNA inhibits transcription of hsp70. HeLa cells transfected with siRNA against SIRT1 or a control siRNA were treated with HS for the indicated times. RT-PCR analysis was performed and fold-increase in hsp70 mRNA abundance was determined by densitometry and normalized to 18S rRNA.
FIG. 1C: SIRT1 siRNA inhibits HSF1 binding to the hsp70 promoter. HeLa cells were treated as described above (2B). ChIP analysis was performed using an HSF1 antibody and qPCR and the results normalized to reactions performed with 1% of input. Experiments were performed in triplicate, and error bars indicate ±SD.

To examine whether SIRT1 influences recruitment of HSF1 to the hsp70 promoter we performed chromatin immunoprecipitation (ChIP) assays with cells transfected with control or SIRT1 siRNA prior to HS (FIG. 1C). In control siRNA-treated cells, binding of HSF1 to the hsp70 promoter occurs rapidly and begins to attenuate at 30 min of heat shock (11) with a gradual decline over a 6-hour period. However, in SIRT1 siRNA-transfected cells, about one fourth as much HSF1 was associated with the promoter throughout the time course. These results support a role for SIRT1 as an in vivo regulator of HSF1 DNA-binding activity and hsp70 expression.

To determine whether HSF1 is a direct target of SIRT1, we examined the acetylation status of HSF1. We transfected 293T cells with vectors encoding a Flag-HSF1 fusion protein and p300 and exposed them to several HSR inducers. Immunoprecipitated HSF1 was analyzed by western blotting with an antibody that binds acetylated lysines. Acetylated HSF1 was not detected in untreated cells but was present in cells exposed to various stress conditions (FIG. 2A). The endogenous acetyltransferase that regulates HSF1 acetylation may be p300/CBP, as overexpression of either p300 or CBP, but not pCAF, resulted in acetylation of HSF1 (FIG. 5A) and p300 was recruited to the hsp70 promoter after HS (FIG. 5B). SIRT1 also binds to the hsp70 promoter under both basal and stress conditions (FIG. 5C).

Figure 2:
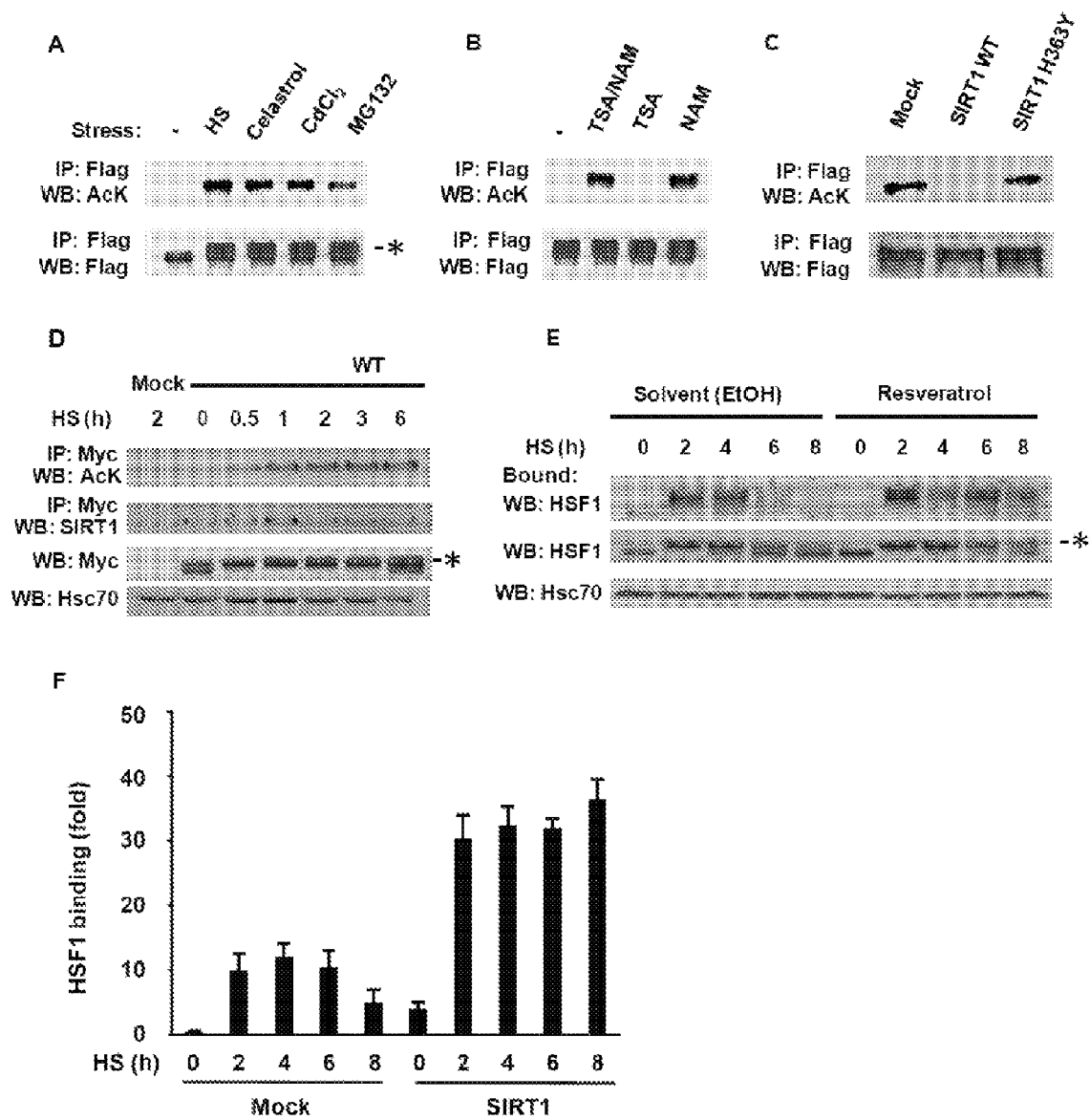
FIG. 2A: Acetylation of HSF1 in response to HSR inducers. 293T cells transfected with Flag-HSF1 and p300 were treated with HS, celastrol, $CdCl_2$ or MG132. Cell lysates were analyzed by acetylation assay using immunoprecipitation and western blotting. Slowly migrating HSF1 due to increased phosphorylation is indicated by an asterisk.
FIG. 2B: Effects of nicotinamide and trichostatin A on HSF1 acetylation. 293T cells transfected with Flag-HSF1 and p300 were treated with trichostatin A (TSA), nicotinamide (NAM), or both, exposed to HS, and cell lysates were analyzed by acetylation assay.
FIG. 2C: Wild-type SIRT1 but not a catalytic mutant inhibits HSF1 acetylation. 293T cells were transfected with Flag-HSF1, p300, and either SIRT1 WT or a SIRT1 H363Y mutant prior to treatment with HS and analysis by acetylation assay.
FIG. 2D: HSF1 acetylation in response to HS. Cos7 cells transfected with Myc-HSF1 were treated with HS for the indicated times and analyzed by acetylation assay. SIRT1 and HSF1 were detected with an antibody to SIRT1 or a Myc antibody. Hsc70 was a loading control.
FIG. 2E: Effects of resveratrol. HeLa cells were treated with solvent (EtOH) or resveratrol prior to HS treatment for the indicated times. Cell extracts were analyzed by oligonucleotide pull-down assay and western blotting. Increased phosphorylation of HSF1 is indicated by an asterisk.
FIG. 2F: SIRT1 overexpression effect on HSF1 DNA binding. 293T cells were transfected with SIRT1 WT and then subjected to HS for the indicated times. ChIP analysis was performed using an HSF1 antibody and qPCR. Experiments in A-G were performed in triplicate and error bars indicate ±SD.

Deacetylases are grouped into three families, with the class I and II HDAC families inhibited by trichostatin A (12) and the NAD+-dependent class III sirtuin family inhibited by nicotinamide (8). Trichostatin A had no effect on deacetylation of HSF1 whereas nicotinamide inhibited deacetylation alone or in the presence of trichostatin A (FIG. 2B). Overexpression of SIRT1 WT, but not a point mutant with impaired NAD-dependent deacetylase activity [SIRT1 H363Y (13)] inhibited HSF1 acetylation (FIG. 2C), supporting a role for SIRT1 in HSF1 function. HSF1 acetylation was not cell-type specific as it was detected in 293T and Cos7 cells, and although HSF1 acetylation was enhanced by p300 overexpression it did not require p300 overexpression (FIG. 2, A and D). The kinetics of HSF1 acetylation do not match the kinetics of HSF1 activation. Acetylation is delayed and persists during the period when HSF1 activity and DNA binding has attenuated (11). Additionally, an HSF1 in which ten potentially phosphorylated serines were replaced with alanines remained competent for acetylation, suggesting that phosphorylation of HSF1 is not a prerequisite for acetylation (FIG. 6).

The persistence of HSF1 acetylation during later time points of the HSR and the co-immunoprecipitation of SIRT1 together with HSF1 (FIG. 2D) led us to investigate whether SIRT1 has a role in attenuation of HSF1 activity. We treated HeLa cells with resveratrol, a small molecule inducer of SIRT1 activity (14), and assayed HSF1 DNA-binding activity in an oligonucleotide-based pull-down assay (15) (FIG. 2E). In cells treated with HS and vehicle alone, HSF1 DNA-binding was induced within two hours and attenuated after six hours. The transient activation of HSF1 was reflected by altered mobility on SDS-PAGE that detects the stress-induced phosphorylated state of HSF1 (16). In contrast, HSF1 in resveratrol-treated cells persisted in a DNA binding-competent and phosphorylated state even after eight hours of continuous HS. In cells overexpressing SIRT1, HSF1 DNA binding was enhanced and attenuation was suppressed as measured by ChIP experiments (FIG. 2F). These results suggest that changes in the abundance and activity of SIRT1 regulate the attenuation of the HSR.

To elucidate the mechanism by which acetylation regulates HSF1 DNA binding, we identified the sites of acetylation on HSF1 by mass spectrometry of peptides from Flag-HSF1 purified from 293T cells. At least nine lysines in HSF1 were acetylated in response to stress (FIG. 7) of which K80, located in the DNA-binding domain, was particularly intriguing because mutations of the corresponding lysine of yeast HSF cause a loss-of-function phenotype (17, 18). Furthermore, analysis of the crystal structure of K. lactis HSF indicated that the lysine corresponding to human HSF1 K80 is located in a short domain that connects the main DNA-binding helix to a flexible and solvent-exposed loop and forms a hydrogen bond with the DNA phosphate backbone (19). Comparative protein modeling of the HSF-HSE crystal structure showed that human HSF1 K80 is in close contact with the DNA backbone (FIG. 8), suggesting that neutralizing the positive charge of lysine by acetylation should interfere with DNA binding.

Figure 3:
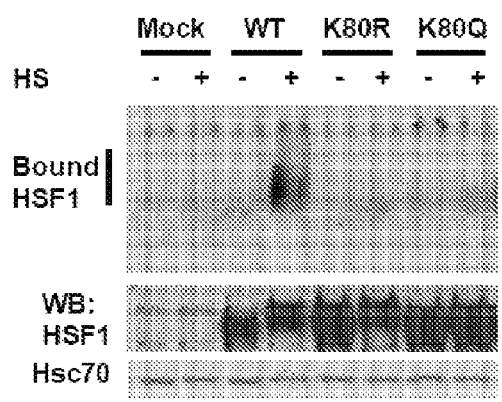
FIG. 3A: Mutation of HSF1 at K80 disrupts DNA-binding activity. EMSA reactions were performed with extracts from hsf1−/− cells transfected with the indicated HSF1 constructs treated with or without HS (upper panel). The EMSA probe contains the proximal HSE from the human hsp70 promoter. Western blot analysis was performed on the same samples to show HSF1 and Hsc70 levels.
FIG. 3B: Mutation of recombinant HSF1 at K80 disrupts DNA-binding ability. EMSA reactions with increasing amounts (5, 20, 40, 80 or 120 ng) of recombinant WT HSF1 or HSF1 K80Q and a probe containing an HSE are shown (upper panel). A sample without (−) HSF1 protein was a control. Western blot analysis was performed on the same samples to show HSF1 expression levels.
FIG. 3C: Failure of HSF1 mutated at K80 to rescue the HSR in hsf1−/− cells. hsf1−/− cells were transfected with the indicated versions of human HSF1 and treated with or without HS. RNA was quantitated using qPCR with primers for the indicated genes. Data are normalized to values obtained for glyceraldehyde 3-phosphate dehydrogenase and are relative to the abundance of each mRNA in WT HSF1 cells treated without HS (value set as 1). Experiments in A-C were performed in triplicate and error bars indicate ±SD.
Figure 3:
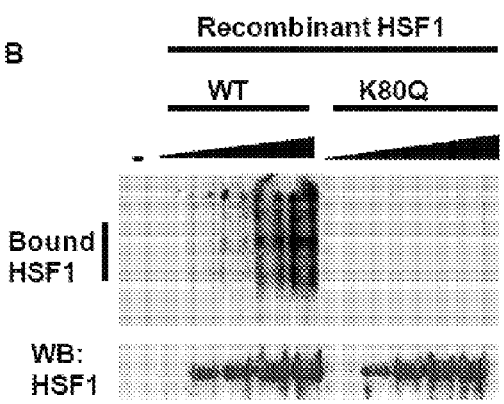
Figure 3:
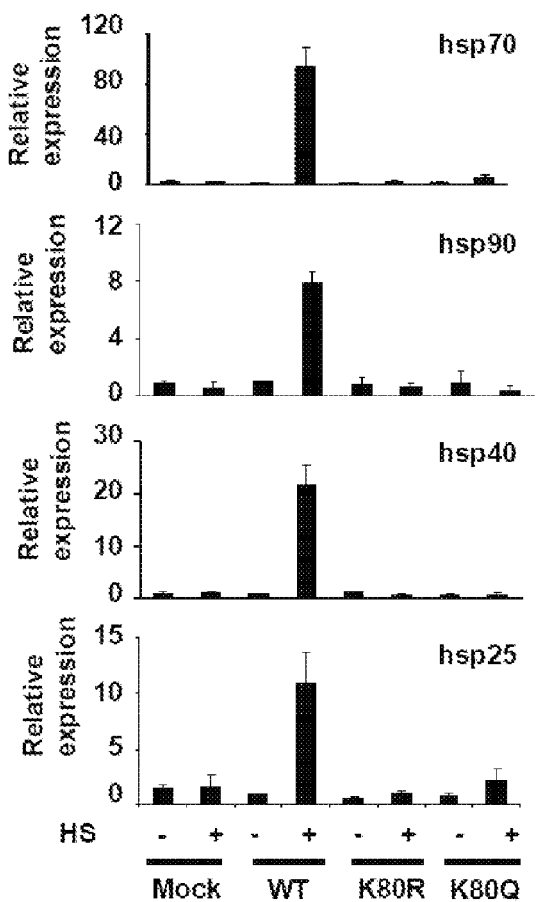

We therefore replaced K80 with a glutamine to mimic constitutive acetylation. In extracts from hsf1−/− fibroblasts (20) transfected with HSF1 WT and HSF1 K80Q expression constructs, the mutant protein failed to bind DNA in an electrophoretic mobility shift assay (EMSA) (FIG. 3A). The K80Q mutant, however, still assembled into HS-induced trimers, a hallmark of the DNA-bound state (FIG. 9). Substitution of other amino acids at K80 (K80R, -A, -H, -N, and -T) also resulted in defective DNA binding (FIG. 3A, FIG. 10). In vitro, recombinant non-acetylated WT HSF1 readily bound to a synthetic HSE, but the K80Q mutant protein did not (FIG. 3B). We introduced WT and the K80 mutants into hsf1−/− fibroblasts and analyzed the HS-induced expression of HSF1 target genes by qPCR. Although WT HSF1 induced expression of hsp mRNAs, HSF1 K80 mutants were non-functional (FIG. 3C). The mutants localized to the nucleus upon HS, but were impaired in the relocalization into nuclear stress bodies that occurs in heat shocked human cells (FIGS. 11-12) (21). An unmodified lysine side chain at residue 80 appears to be required for HSF1 HSE-binding ability, relocalization into nuclear stress bodies, and expression of target genes. Therefore, we propose that acetylation of HSF1 K80 causes the regulated release of the HSF1 trimers from DNA and thus represents a regulatory step in the attenuation of the HSR (FIG. 13).

Figure 4:
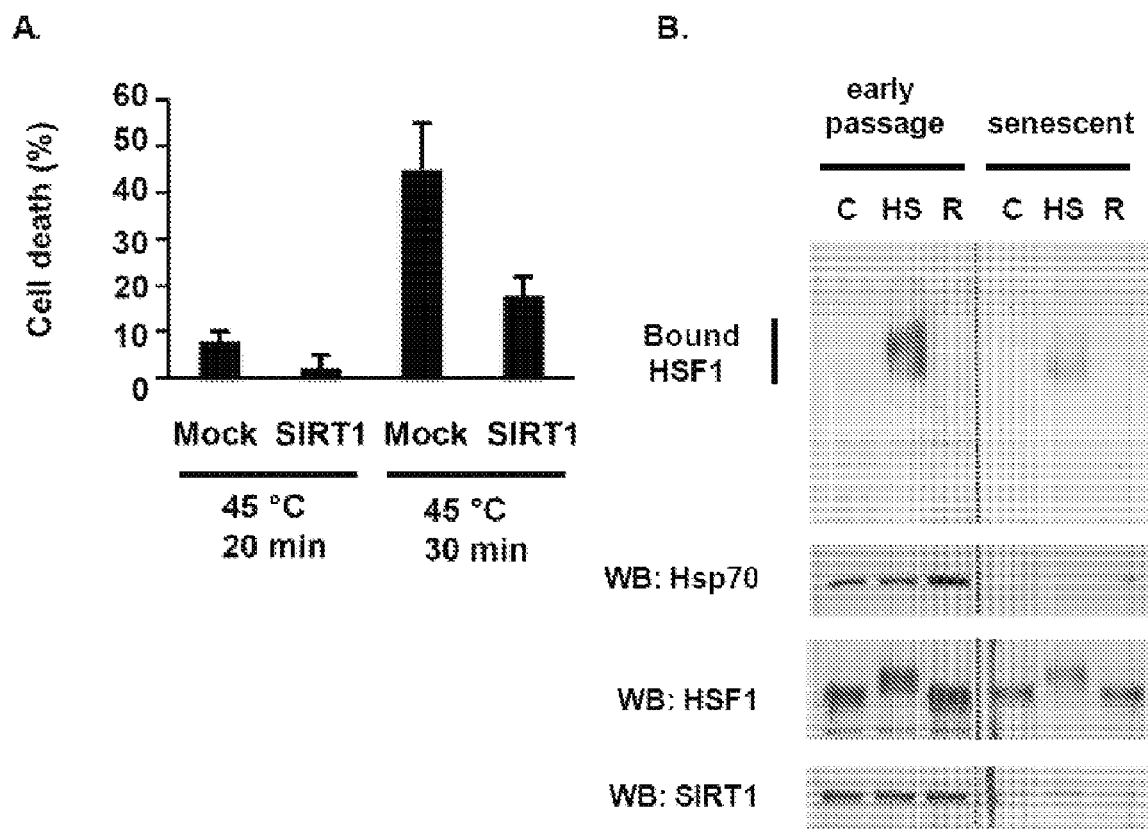
FIG. 4A: Protection of cells from severe stress by overexpressed SIRT1. 293T cells were transfected with empty vector (Mock) or SIRT1 and treated with a 45° C. HS for the indicated times, followed by recovery at 37° C. 24 hours later, cell death was determined by trypan blue uptake. The experiment was performed three times in triplicate and error bars indicate ±SD.
FIG. 4B: Correlation of the age-dependent decline in the HSR with decreased abundance of SIRT1. Cell extracts from early passage (passage 21) and senescent (passage 44) WI-38 fibroblasts were treated with HS or HS followed by a three hour recovery at 37° C. (R) and analyzed by EMSA with a probe containing an HSE (upper panel). Western blot analysis was done on the same samples to show Hsp70, HSF1 and SIRT1 expression levels (lower panels).

To verify the biological significance of the regulation of the HSR by SIRT1, we used an assay of stress resistance in which the expression of chaperones confers increased thermotolerance (22). 293T cells were transfected with or without SIRT1, exposed to a 45° C. HS for 20 or 30 min, allowed to recover for twenty-four hours, and analyzed for cell death. As expected, the 45° C. HS resulted in cell death that increased with treatment time (FIG. 4A). At both timepoints, the cells overexpressing SIRT1 had about one third as many cells undergo cell death (FIG. 4A). To examine whether age-regulated changes in SIRT1 affect HSF1 activity and the HSR, we used human WI-38 fibroblasts that have been widely used in studies on molecular changes in the aging process. When comparing early and late passage numbers, we found that aging resulted in a decreased HSR and reduced activation of HSF1 DNA-binding activity that correlated with the reduced abundance of SIRT1 (FIG. 4B).

The finding that SIRT1 regulates HSF1 complements previous observations on the role of HSF1 in regulating lifespan (4, 5). HSF1 appears to be at the hub of a regulatory network in which cell nutrition, stress, and lifespan are linked. Many SIRT1-regulated transcription factors, including FOXO3, p53, and NF-κB, have important roles in cellular stress responses (7, 23, 24). The addition of HSF1 to this stress regulatory network emphasizes the central role of protein homeostasis in SIRT1-mediated cellular protection (FIG. 14) and may link the molecular response of the HSR to metabolic demands. A consistent observation in cell-based and animal studies has been the aging-related decline of the HSR (22), which may result, at least in part, from SIRT1 control of HSF1 activity. At the organismal level, we expect that regulation of HSF1 target genes may be influenced by diet and nutrition.

Materials & Methods

Constructs, Antibodies and Reagents mHSF1-Flag and hHSF1-Myc have been described earlier (25,26). HSF1 point mutants were created by QuikChange Site-directed mutagenesis (Stratagene) and confirmed by sequencing. For the Myc-HSF1 ten serine mutant, phosphorylated serine residues S230, S303, S307, S314, S319, S320, S338, S363, S368 and S369 (Ref. 27 and our unpublished data) were all mutated to alanines SIRT1 WT and the H363Y mutant expression constructs were kindly provided by Dr. Tony Kouzarides (University of Cambridge) and the p300 expression construct from Dr. David Livingston (Harvard University). Antibodies used in this study are α-Flag M2 (Sigma), α-AcK (Cell Signaling 9441), α-HSF1 (4), α-SIR2 (Upstate Biotech #07-131), α-Myc (Clontech) and α-p300 (Santa Cruz). Chemical compounds used are nicotinamide (Sigma), trichostatin A (Upstate), EGS (Sigma), celastrol (GAIA Chemical Corporation), $CdCl_2$ (Sigma) and MG132 (Calbiochem).

Cell Culture, Transfections and Treatment Conditions

All cells were maintained at 37° C. in a humidified 5% $CO_2$ atmosphere. K562 cells were cultured in RPMI 1640 medium supplemented with 10% FCS and antibiotics (penicillin and streptomycin). 293T, HeLa, Cos7 and WI-38 cells were cultured in DMEM supplemented with 10% FCS and antibiotics. hsf1−/− mouse embryonic fibroblasts (29) were cultured in DMEM with 10% FCS, 10 mM non-essential amino acids, 0.96 µl of 2-mercaptoethanol per 100 ml, and antibiotics. 293T cells were transfected using Polyfect (Qiagen) according to the manufacturer's instructions. K562, Cos7 and hsf1−/− cells were transfected by electroporation with a Gene Pulser electroporator (Bio-Rad). Heat shock was induced by submersion of cells in a prewarmed circulating water bath at 42° C. for 1 hour. Celastrol treatment was at a concentration of 5 µM for 1 hour, $CdCl_2$ treatment was at 50 µM for 6 hours and MG132 was at 20 µM for 6 hours. Trichostatin A was added to cells overnight at 1 mM, nicotinamide overnight at 5 mM and resveratrol for 40 hours at 50 µM.

siRNA Transfections

HeLa cells were transfected with Oligofectamine (Invitrogen) according to the manufacturer's protocol, using 200 nM of Dharmacon SmartPool SIRT1 siRNA. Twenty-four hours later, cells were split and transfected again. RNA was isolated using Trizol 48 hours after the second transfection. Primers were used to verify knockdown of SIRT1.

Acetylation Assays 293T or Cos7 cells were transfected with Flag-HSF1 or Myc-HSF1 and p300, and then treated with or without nicotinamide prior to treatment with various stresses. Cell lysates were subjected to immunoprecipitation with a Flag antibody or Myc antibody, and acetylated HSF1 was detected by western blotting with an antibody that recognizes acetylated lysines.

Chromatin Immunoprecipitation (ChIP)

ChIP reactions were performed essentially as previously described (30). Samples generated from HeLa cells ($3\times10^7$) were immunoprecipitated with 10 µl α-HSF1 (28) at 4° C.

overnight. Primers used for the hsp70.1 promoter (GenBank Acc# M11717) and surround the proximal HSE. Results were normalized to reactions performed with 1% of input.

Purification of HSF1 from 293T Cells 293T cells were transfected with mHSF1-Flag with or without CMV-p300 as indicated with Polyfect (Qiagen) according to the manufacturer's protocol. Cells were treated with trichostatin A or nicotinamide as indicated 4 hours prior to performing stress treatments. Cell pellets were then harvested and lysed in RIPA buffer. mHSF1-Flag was immunoprecipitated with α-Flag M2 affinity gel beads (Sigma F2426) and eluted with Flag peptide. Samples were separated by SDS-PAGE prior to western blot analysis.

Mass Spectrometry Analysis

Purified mHSF1-Flag was obtained as described above from 293T cells transfected with mHSF1-Flag and CMV-p300 and treated with 1 μM trichostatin A and 5 mM nicotinamide for 18 hours prior to HS or celastrol treatment. Immunoprecipitated protein was separated by SDS-PAGE, excised from the gel, digested with trypsin, and subjected to tandem mass spectrometric analysis by a hybrid quadrupole time-of-flight instrument (QSTAR, Applied Biosystems, Foster City, Calif.) equipped with a nanoelectrospray source. MS/MS spectra were searched against the IPI mouse sequence database (68,222 entries; version 3.15) using Mascot (Matrix Science, Boston, Mass.; version 1.9.05) and X! Tandem (www.thegpm.org; version 2006.04.01.2) database search algorithms. Mascot and X! Tandem were searched with a fragment and precursor ion mass tolerance of 0.3 Da assuming the digestion enzyme trypsin with the possibility of one missed cleavage. Carbamidomethylation of cysteine was included as a fixed modification whereas methionine oxidation, N-terminal protein and lysine acetylation were included as variable modifications in the database search. Peptide identifications were accepted at greater than 95.0% probability as determined by the Peptide Prophet algorithm (31) and validated by manual inspection of the MS/MS spectra.

Recombinant Proteins

Murine His-HSF1 was produced in the *Escherichia coli* strain BL-21 as previously described (32). Harvested bacteria were resuspended in cold lysis buffer [50 mM Tris-HCl (pH 7.4), 140 mM NaCl, 10% glycerol] and lysed with 1 mg/ml lysozyme at room temperature for 15 minutes. After addition of 1 mM PMSF (phenylmethylsulfonyl fluoride), 1 mM DTT (dithiotreitol) and EDTA-free protease inhibitor cocktail (Roche), lysates were sonicated and incubated with Talon metal affinity resin (Clontech) for 2 hours at 4° C. Resins were washed extensively with lysis buffer containing 0.5% Triton X-100 and eluted in 50 mM NaAc (pH 5.0), 300 mM NaCl, 200 mM imidazole. Eluted proteins were dialyzed against PBS and diluted into equal amounts.

Electrophoretic Mobility Shift Assay (EMSA)

Buffer C extracts (15 μg) from WI-38 cells and transfected hsf1−/− cells or recombinant HSF1 proteins were incubated with a $^{32}$P-labeled oligonucleotide representing the proximal HSE from the human hsp70 promoter (33). The protein-DNA complexes were analyzed on a 4% native polyacrylamide gel.

Oligonucleotide Pull-Down Assay

The assay was performed essentially as previously described (32), with slight modifications. HeLa cells were lysed in cold lysis buffer [25 mM HEPES (pH 7.4), 100 mM NaCl, 5 mM EDTA, 20 mM p-glycerophosphate, 20 mM p-nitro-phenyl-phosphate, 0.5% Triton X-100, 20 mM 100 μM sodium orthovanadate] containing protease inhibitors. Cell extracts were incubated with 1 μg of biotinylated oligonucleotide (Oligomer, Helsinki, Finland) and proteins were allowed to bind the oligonucleotide for 30 minutes at room temperature. The oligonucleotides were precipitated with UltraLink streptavidin beads (Pierce) for 1 h at 4° C. Bound fractions were washed three times with wash buffer [20 mM Tris-HCl (pH 7.5), 1 mM EDTA, 10% glycerol, 0.1% Triton X-100], eluted with denaturing buffer and analyzed by western blotting.

RT-PCR Analysis

HeLa cells were harvested and RNA was generated using the Trizol reagent (Gibco-BRL, Gaithersburg, Md.) according to the manufacturer's instructions. The following proteins were made using a reverse transcription reaction and PCR: hsp90, hsp70, hsp40, hsp25, hsp27, 18S, and gapdh.

Quantitative Real-Time RT-PCR Analysis

Analysis of hsp70 and hsp25 gene expression in transfected hsf1−/− cells was performed essentially as described (34). Briefly, RNA was isolated using the RNeasy kit (Qiagen). For each sample, 1 μg of RNA was treated with RQ1 DNase (Promega) and reverse-transcribed by using Moloney murine leukemia virus RNase H (−) (Promega). ABsolute QPCR ROX Mix (Advanced Biotechnologies) was used to prepare the reaction mixes. Relative quantities of hsp mRNAs were normalized against gapdh. All reactions were made in triplicates with samples derived from three biological repeats.

Confocal Microscopy

HeLa cells growing on coverslips were kept at the control temperature or heat shocked for 1 hour at 42° C. Cells were washed with PBS and simultaneously fixed and permeabilized in 3.7% paraformaldehyde containing 0.5% Triton X-100. Cells were washed twice with PBS and incubated in blocking solution (20% normal goat serum in PBS-0.05% Tween 20) for 1 hour. Primary antibodies [rabbit a-HSF1 (11), mouse α-Myc (Sigma)] were used at a 1:500 dilution in 5% BSA in PBS-0.05% Tween 20) overnight at 4° C. After three washes with PBS-0.05% Tween 20, primary antibodies were detected using secondary goat α-mouse IgG (Rhodamine Red-X and Alexa Fluor 488, Molecular Probes) or goat α-rabbit IgG (Alexa Fluor 546, Molecular 488, Molecular Probes). All secondary antibodies were used at 1:500 dilutions in 5% BSA in PBS-0.05% Tween 20 for 1 hour at room temperature. After three washes, cells were mounted on slides in Vectashield containing DAPI (4',6'-diamidino-2-phenylindole; Vector Laboratories) and analyzed using a Zeiss LSM510 META confocal microscope. Images were further processed using Adobe Photoshop software.

Crosslinking

Cells were kept at 37° C. or heat shocked for 15 minutes at 42° C. and lysed in cold lysis buffer [25 mM HEPES (pH 7.4), 100 mM NaCl, 5 mM EDTA, 0.5% Triton X-100, 20 mM β-glycerophosphate, 20 mM p-nitro-phenyl-phosphate, 100 μM sodium orthovanadate, 0.5 mM phenylmethylsulfonyl fluoride, 1 mM dithiothreitol, protease inhibitor cocktail] and centrifuged at 4° C. for 10 minutes at 15,000×g. 100 μg protein were crosslinked with 2 mM EGS [ethylene glycol bis(succinimidylsuccinate)] at room temperature for 15 minutes. After quenching of crosslinking by addition of 100 mM glycine, samples were boiled in denaturing buffer and analyzed on a 5% SDS-PAGE gel followed by western blotting.

Heat Stress Resistance Assay 293T cells transfected with a vector control (Mock) or SIRT1 were compared for resistance to a 45° C. heat shock. Cells were submerged in a 45° C. water bath for 20 or 30 min and then allowed to recover at 37° C. Cells were assayed for percent cell death by trypan blue uptake 24 hours later.

References

1. J. Anckar, L. Sistonen, *Adv Exp Med Biol* 594, 78 (2007).
2. Y. Shi, D. D. Mosser, R. I. Morimoto, *Genes Dev* 12, 654 (1998).
3. S. K. Rabindran, J. Wisniewski, L. Li, G. C. Li, C. Wu, *Mol Cell Biol* 14, 6552 (1994).
4. A. L. Hsu, C. T. Murphy, C. Kenyon, *Science* 300, 1142 (2003).
5. J. F. Morley, R. I. Morimoto, *Mol Biol Cell* 15, 657 (2004).
6. S. Imai, C. M. Armstrong, M. Kaeberlein, L. Guarente, *Nature* 403, 795 (2000).
7. A. Brunet et al., *Science* 303, 2011 (2004).
8. K. J. Bitterman, R. M. Anderson, H. Y. Cohen, M. Latorre-Esteves, D. A. Sinclair, *J Biol Chem* 277, 45099 (2002).
9. Materials and methods are available as supporting material on *Science* Online.
10. N. Dali-Youcef et al., *Ann Med* 39, 335 (2007).
11. M. P. Kline, R. I. Morimoto, Mol Cell Biol 17, 2107 (1997).
12. M. Yoshida, M. Kijima, M. Akita, T. Beppu, *J Biol Chem* 265, 17174 (1990).
13. E. Langley et al., *EMBO J* 21, 2383 (2002).
14. K. T. Howitz et al., *Nature* 425, 191 (2003).
15. J. Anckar et al., *Mol Cell Biol* 26, 955 (2006).
16. K. D. Sarge, S. P. Murphy, R. I. Morimoto, *Mol Cell Biol* 13, 1392 (1993).
17. S. T. Hubl, J. C. Owens, H. C. Nelson, *Nat Struct Biol* 1, 615 (1994).
18. F. A. Torres, J. J. Bonner, *Mol Cell Biol* 15, 5063 (1995).
19. O. Littlefield, H. C. Nelson, *Nat Struct Biol* 6, 464 (1999).
20. D. R. McMillan, X. Xiao, L. Shao, K. Graves, I. J. Benjamin, *J Biol Chem* 273, 7523 (1998).
21. C. Jolly et al., *J Cell Biol* 156, 775 (2002).
22. K. C. Kregel, *J Appl Physiol* 92, 2177 (2002).
23. H. Vaziri et al., *Cell* 107, 149 (2001).
24. F. Yeung et al., *Embo J* 23, 2369 (2004).
25. J. Cotto, S. Fox, R. Morimoto, *J Cell Sci* 110 (Pt 23), 2925 (1997).
26. C. I. Holmberg et al., *Embo J* 20, 3800 (2001).
27. T. Guettouche, F. Boellmann, W. S. Lane, R. Voellmy, *BMC Biochem* 6, 4.
28. S. D. Westerheide et al., *J Biol Chem* 279, 56053 (2004).
29. D. R. McMillan, X. Xiao, L. Shao, K. Graves, I. J. Benjamin, *J Biol Chem* 273, 7523 (1998).
30. G. W. Beresford, J. M. Boss, *Nat Immunol* 2, 652 (2001).
31. A. Keller, A. I. Nesvizhskii, E. Kolker, R. Aebersold, *Anal Chem* 74, 5383 (2002).
32. J. Anckar et al., *Mol Cell Biol* 26, 955 (2006).
33. D. D. Mosser, N. G. Theodorakis, R. I. Morimoto, *Mol Cell Biol* 8, 4736 (1988).
34. V. Hietakangas et al., *Proc Natl Acad Sci USA* 103, 45 (2006).
35. C. I. Holmberg, S. A. Illman, M. Kallio, A. Mikhailov, L. Sistonen, *Cell Stress Chaperones* 5, 219 (2000).
36. J. Y. Kim, K. W. Kim, H. J. Kwon, D. W. Lee, J. S. Yoo, *Anal Chem* 74, 5443 (2002).
37. O. Littlefield, H. C. Nelson, *Nat Struct Biol* 6, 464 (1999).
38. S. K. Rabindran, R. I. Haroun, J. Clos, J. Wisniewski, C. Wu, *Science* 259, 230 (1993).

Example 2

Activation of SIRT1 Synergizes with Celastrol, a Small Molecule Activator of the Heat Shock Response A number of activators of the heat shock response have been identified [2]. Some of the small molecule heat shock activators are being investigated for therapeutic utility in protein misfolding diseases. It would be beneficial to use the small molecules at the lowest dose possible for activating the heat shock response, as the separation between the therapeutic dose and the toxic dose is often small. The present set of experiments show that activating SIRT1 synergizes with inducers of the heat shock response, thereby allowing the induction of the response with lower levels of heat or celastrol, a small molecule activator of the heat shock response [3].

The current strategies for treating diseases of protein misfolding through activating the heat shock response involve treating the organism with a high level of heat or with amounts of small molecules that are sufficient for inducing this response. In some cases, the levels of heat or compound required to induce the heat shock response can also result in cellular damage or toxicity. This amount of heat shock or small molecule compound required to induce the heat shock response can be lowered by activating SIRT1 at the same time. As described in Example 1, SIRT1 was found to activate the heat shock response in combination with heat shock by preventing the attenuation step of the HSF1 activity cycle [1]. The present study shows that activation of SIRT1 synergizes with heat shock and small molecule activators of the heat shock response to lower the heat shock temperature or EC50 of the compounds required for robust activation of the response.

As shown in FIGS. 16 and 17, the SIRT1 activator resveratrol [4] synergizes with both heat shock and celastrol to induce the heat shock response as determined by a reporter assay. As a tool to probe activation of the heat shock response, a HeLa stable cell line containing sequences from −188 to +150 of the human hsp70.1 promoter fused to luciferase (FIG. 15, [4]) was created. Using this cell line, it was investigated whether activation of SIRT1 with resveratrol could lower the temperature threshold for activation of the heat shock response. As shown in FIG. 16, a 42° C. heat shock induced the reporter by 15-fold, while a 41° C. heat shock induced the reporter by only 5-fold. Pretreatment of the cells with resveratrol increased the reporter induction at both temperatures, suggesting that activation of SIRT1 can synergize with heat to activate the heat shock response and allow a lower temperature to induce a response. Similarly, as shown in FIG. 17, it was found that resveratrol can synergize with celastrol, a known heat shock response inducer with an EC50 of 5 μM [4]. While 1 μM of celastrol alone only activated the reporter by 2-fold, the combination of resveratrol and 1 μM celastrol induced robust reporter activation of over 40-fold.

The hsp70.1pr-luc HeLa stable cell line contains hsp70.1 promoter sequence from −188 to +150 and includes the proximal heat shock element (HSE). The creation of this cell line is described in Westerheide et al. (2004). *Celastrols as inducers of the heat shock response and cytoprotection*. J Biol Chem, 2004. 279(53): p. 56053-60, the contents of which are incorporated by reference herein.

HeLa hsp70.1pr-luc cells were plated in white 96-well plates at a density of $15 \times 10^3$ cells per well in 100 ul of DMEM medium plus 10% fetal bovine serum. The cells were incubated for 20 hours at 37° C., 5% $CO_2$ prior to treatment with or without resveratrol. Resveratrol was diluted in EtOH and added to the cells at 0.5 uM. Two hours later, the cells were then heat shocked at the indicated temperatures by submerging in a water bath for 1 hour. After the heat shock treatment, the plates were put back into the incubator at 37° C., 5% $CO_2$, and were incubated for 18 hours prior to luciferase assay.

HeLa hsp70.1pr-luc cells were plated in white 96-well plates at a density of $15 \times 10^3$ cells per well in 100 ul of DMEM medium plus 10% fetal bovine serum. The cells were incubated for 20 hours at 37° C., 5% $CO_2$ prior to treatment with or without resveratrol. Resveratrol was diluted in EtOH and added to the cells at 1.0 uM. Two hours later, the cells were then treated with or without 1 mM celastrol as indicated (celastrol was dissolved in DMSO). 18 hours after the celastrol addition, the cells were assayed by luciferase assay.

Figure Legends:

FIG. 16. The SIRT1 activator resveratrol synergizes with heat shock to activate the hsp70.1pr-luc reporter.

FIG. 17. The SIRT1 activator resveratrol synergizes with celastrol to activate the hsp70.1pr-luc reporter.

1. Westerheide, S. D., et al., *Stress-inducible regulation of heat shock factor 1 by the deacetylase SIRT1*. Science, 2009. 323(5917): p. 1063-6.
2. Westerheide, S. D., et al., *Triptolide, an inhibitor of the human heat shock response that enhances stress-induced cell death*. J Biol Chem, 2006.
3. Westerheide, S. D., et al., *Celastrols as inducers of the heat shock response and cytoprotection*. J Biol Chem, 2004. 279(53): p. 56053-60.
4. Howitz, K. T., et al., *Small molecule activators of sirtuins extend Saccharomyces cerevisiae lifespan*. Nature, 2003. 425(6954): p. 191-6.

While this invention has been particularly shown and described with references to preferred embodiments thereof, it will be understood by those skilled in the art that various changes in form and details may be made therein without departing from the scope of the invention encompassed by the appended claims.

```
                                                                SEQ ID NO: 1
   1 mdlpvgpgaa gpsnvpaflt klwtivsdpd tdalicwsps gnsfhvfdqg qfakevlpky
  61 fkhnnmasfv rqlnmygfrk vvhieqgglv kperddtefq hpcflrgqeq llenikrkvt
 121 systlksedi kirqdsvtkl ltdvqlmkgk qecmdsklla mkhenealwr evaslrqkha
 181 qqqkvvnkli qflislvqsn rilgvkrkip lmlndsgsah smpkysrqfs lehvhgsgpy
 241 sapspaysss slyapdavas sgpiisdite lapaspmasp ggsiderpls ssplvrvkee
 301 ppsppqsprv eeaspgrpss vdtllsptal idsilresep apasvtaltd arghtdtegr
 361 ppsppptstp ekclsvacld knelsdhlda mdsnldnlqt mlsshgfsvd tsalldlfsp
 421 svtvpdmslp dldsslasiq ellspqeppr ppeaensspd sgkqlvhyta qplflldpgs
 481 vdtgsndlpv lfelgegsyf segdgfaedp tislltgsep pkakdptvs SEQ ID NO: 2
   1 madeaalalq pggspsaaga dreaasspag eplrkrprrd gpglerspge pggaaperev
  61 paaargcpga aaaalwreae aeaaaaggeq eaqataaage gdngpglqgp sreppladnl
 121 ydedddege eeeeaaaaai gyrdnllfgd eiitngfhsc esdeedrash asssdwtprp
 181 rigpytfvqq hlmigtdprt ilkdllpeti pppelddmtl wqivinilse ppkrkkrkdi
 241 ntiedavkll qeckkiivlt gagvsyscgi pdfrsrdgiy arlavdfpdl pdpqamfdie
 301 yfrkdprpff kfakeiypgq fqpslchkfi alsdkegkll rnytqnidtl eqvagiqrii
 361 qchgsfatas clickykvdc eavrgdifnq vvprcprcpa deplaimkpe ivffgenlpe
 421 qfhramkydk devdllivig sslkvrpval ipssiphevp qilinreplp hlhfdvellg
 481 dcdviinelc hrlggeyakl ccnpvklsei tekpprtqke laylselppt plhvsedsss
 541 pertsppdss vivtlldqaa ksnddldvse skgcmeekpq evqtsrnves iaeqmenpdl
 601 knvgsstgek nertsvagtv rkcwpnrvak eqisrrldgn qylflppnry ifhgaevysd
 661 seddvlssss cgsnsdsgtc qspsleepme deseieefyn gledepdvpe raggagfgtd
 721 gddqeainea isvkqevtdm nypsnks
```

---

What is claimed is:

1. A method of modulating the activity of heat shock transcription factor 1 (HSF1) in a human cell comprising modifying acetylation of a lysine residue in the DNA binding domain of the HSF1, wherein the lysine residue is lysine 80 (HSF1 K80).

2. The method of claim 1, wherein the activity of HSF1 is increased by inhibiting the acetylation of the lysine residue.

3. The method of claim 1, wherein the activity of HSF1 is decreased by promoting the acetylation of the lysine residue.

4. The method of claim 2, wherein the acetylation of HSF1 K80 is inhibited by administering to the cell an effective amount an agent that inhibits acetylation of HSF1 K80, wherein the agent is selected from the group consisting of an isolated sirtuin, a sirtuin activating agent and a histone acetyltransferase (HAT) inhibiting agent.

5. The method of claim 4, wherein the isolated sirtuin is sirtuin 1 (SIRT1).

6. The method of claim 4, wherein a SIRT1 activating agent is administered.

7. The method of claim 4, wherein a HAT inhibiting agent is administered.

8. The method of claim 3, wherein the acetylation of HSF1 K80 is promoted by administering to the cell an agent that promotes acetylation of HSF1 K80, wherein the agent is selected from the group consisting of a sirtuin inhibiting agent and a HAT activating agent.

9. The method of claim 8, wherein a SIRT1 inhibiting agent is administered.

10. The method of claim 9, wherein the SIRT1 inhibiting agent is a small molecule, nucleic acid or antibody.

11. A method of increasing the activity of HSF1 in a subject in need thereof comprising inhibiting the acetylation of a lysine residue in the DNA binding domain of the HSF1 in a cell of said subject, wherein the lysine residue is HSF1 K80 or a corresponding conserved lysine residue.

12. The method of claim 11, wherein an agent that inhibits the acetylation of HSF1 K80 is administered to said subject in an effective amount.

13. The method of claim 12, wherein the agent that inhibits the acetylation of HSF1 K80 is an isolated sirtuin, a sirtuin activating agent or a HAT inhibiting agent.

14. The method of claim 11, wherein the subject is a human.

15. The method of claim 14, wherein a SIRT1 activating agent is administered.

16. The method of claim 14, wherein a HAT inhibiting agent is administered.

17. A method of decreasing the activity of HSF1 in a subject in need thereof comprising promoting the acetylation of a lysine residue in the DNA binding domain of HSF1 in a cell of said subject, wherein the lysine residue is HSF1 K80.

18. The method of claim 17, wherein an agent that promotes acetylation of HSF1 K80 or the corresponding conserved lysine residue is administered to said subject.

19. The method of claim 18, wherein the acetylation of HSF1 K80 is promoted by administering to said subject a sirtuin inhibiting agent or a HAT activating agent.

20. The method of claim 19, wherein the sirtuin inhibiting agent is a SIRT1 inhibiting agent.

21. The method of claim 17, wherein the subject is a human.

* * * * *

SEQUENCE LISTING

<160> NUMBER OF SEQ ID NOS: 9

<210> SEQ ID NO 1
<211> LENGTH: 529
<212> TYPE: PRT
<213> ORGANISM: Homo Sapien

<400> SEQUENCE: 1

```
Met Asp Leu Pro Val Gly Pro Gly Ala Ala Gly Pro Ser Asn Val Pro
 1               5                  10                  15

Ala Phe Leu Thr Lys Leu Trp Thr Leu Val Ser Asp Pro Asp Thr Asp
                20                  25                  30

Ala Leu Ile Cys Trp Ser Pro Ser Gly Asn Ser Phe His Val Phe Asp
            35                  40                  45

Gln Gly Gln Phe Ala Lys Glu Val Leu Pro Lys Tyr Phe Lys His Asn
        50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
            180                 185                 190

Leu Ile Ser Leu Val Gln Ser Asn Arg Ile Leu Gly Val Lys Arg Lys
        195                 200                 205

Ile Pro Leu Met Leu Asn Asp Ser Gly Ser Ala His Ser Met Pro Lys
210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
        275                 280                 285

Leu Ser Ser Ser Pro Leu Val Arg Val Lys Glu Glu Pro Pro Ser Pro
290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
                325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Pro Thr Ser
        355                 360                 365

Thr Pro Glu Lys Cys Leu Ser Val Ala Cys Leu Asp Lys Asn Glu Leu
370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                405                 410                 415
```

-continued

```
Leu Phe Ser Pro Ser Val Thr Val Pro Asp Met Ser Leu Pro Asp Leu
                420                 425                 430

Asp Ser Ser Leu Ala Ser Ile Gln Glu Leu Leu Ser Pro Gln Glu Pro
            435                 440                 445

Pro Arg Pro Pro Glu Ala Glu Asn Ser Ser Pro Asp Ser Gly Lys Gln
    450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
    515                 520                 525

Ser

<210> SEQ ID NO 2
<211> LENGTH: 747
<212> TYPE: PRT
<213> ORGANISM: Homo Sapien

<400> SEQUENCE: 2

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
                20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
    115                 120                 125

Gly Glu Glu Glu Glu Ala Ala Ala Ala Ile Gly Tyr Arg Asp
130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
    195                 200                 205

Thr Ile Pro Pro Pro Glu Leu Asp Asp Met Thr Leu Trp Gln Ile Val
210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255
```

-continued

Ile Val Leu Thr Gly Ala Gly Val Ser Val Ser Cys Gly Ile Pro Asp
              260                 265                 270

Phe Arg Ser Arg Asp Gly Ile Tyr Ala Arg Leu Ala Val Asp Phe Pro
              275                 280                 285

Asp Leu Pro Asp Pro Gln Ala Met Phe Asp Ile Glu Tyr Phe Arg Lys
290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
              325                 330                 335

Gly Lys Leu Leu Arg Asn Tyr Thr Gln Asn Ile Asp Thr Leu Glu Gln
              340                 345                 350

Val Ala Gly Ile Gln Arg Ile Ile Gln Cys His Gly Ser Phe Ala Thr
              355                 360                 365

Ala Ser Cys Leu Ile Cys Lys Tyr Lys Val Asp Cys Glu Ala Val Arg
              370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
              405                 410                 415

Asn Leu Pro Glu Gln Phe His Arg Ala Met Lys Tyr Asp Lys Asp Glu
              420                 425                 430

Val Asp Leu Leu Ile Val Ile Gly Ser Ser Leu Lys Val Arg Pro Val
              435                 440                 445

Ala Leu Ile Pro Ser Ser Ile Pro His Glu Val Pro Gln Ile Leu Ile
              450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
              485                 490                 495

Tyr Ala Lys Leu Cys Cys Asn Pro Val Lys Leu Ser Glu Ile Thr Glu
              500                 505                 510

Lys Pro Pro Arg Thr Gln Lys Glu Leu Ala Tyr Leu Ser Glu Leu Pro
              515                 520                 525

Pro Thr Pro Leu His Val Ser Glu Asp Ser Ser Ser Pro Glu Arg Thr
530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
              565                 570                 575

Glu Lys Pro Gln Glu Val Gln Thr Ser Arg Asn Val Glu Ser Ile Ala
              580                 585                 590

Glu Gln Met Glu Asn Pro Asp Leu Lys Asn Val Gly Ser Ser Thr Gly
              595                 600                 605

Glu Lys Asn Glu Arg Thr Ser Val Ala Gly Thr Val Arg Lys Cys Trp
              610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
              645                 650                 655

Val Tyr Ser Asp Ser Glu Asp Asp Val Leu Ser Ser Ser Ser Cys Gly
              660                 665                 670

Ser Asn Ser Asp Ser Gly Thr Cys Gln Ser Pro Ser Leu Glu Glu Pro
              675                 680                 685

```
Met Glu Asp Glu Ser Glu Ile Glu Glu Phe Tyr Asn Gly Leu Glu Asp
        690                 695                 700
Glu Pro Asp Val Pro Glu Arg Ala Gly Gly Ala Gly Phe Gly Thr Asp
705                 710                 715                 720
Gly Asp Asp Gln Glu Ala Ile Asn Glu Ala Ile Ser Val Lys Gln Glu
                    725                 730                 735
Val Thr Asp Met Asn Tyr Pro Ser Asn Lys Ser
                740                 745

<210> SEQ ID NO 3
<211> LENGTH: 211
<212> TYPE: PRT
<213> ORGANISM: Homo sapiens

<400> SEQUENCE: 3

His Val Phe Asp Gln Gly Gln Phe Ala Lys Glu Val Leu Pro Lys Tyr
 1               5                  10                  15
Phe Lys His Asn Asn Met Ala Ser Phe Val Arg Gln Leu Asn Met Tyr
                20                  25                  30
Gly Phe Arg Lys Val Val His Ile Glu Gln Gly Gly Leu Val Lys Pro
             35                  40                  45
Glu Arg Asp Asp Thr Glu Phe Gln His Pro Cys Phe Leu Arg Gly Gln
 50                  55                  60
Glu Gln Leu Leu Glu Asn Ile Lys Arg Lys Val Thr Ser Val Ser Thr
 65                  70                  75                  80
Leu Lys Ser Glu Asp Ile Lys Ile Arg Gln Asp Ser Val Thr Lys Leu
                 85                  90                  95
Leu Thr Asp Val Gln Leu Met Lys Gly Lys Gln Glu Cys Met Asp Ser
                100                 105                 110
Lys Leu Leu Ala Met Lys Leu Ile Ser Leu Val Gln Ser Asn Arg Ile
            115                 120                 125
Leu Gly Val Lys Arg Lys Ile Pro Leu Met Leu Asn Asp Ser Gly Ser
        130                 135                 140
Ala His Ser Met Pro Lys Tyr Ser Arg Gln Phe Ser Leu Glu His Val
145                 150                 155                 160
His Gly Ser Gly Pro Tyr Ser Ala Pro Ser Pro Ala Tyr Ser Ser Ser
                165                 170                 175
Pro Gly Gly Ser Ile Asp Glu Arg Pro Leu Ser Ser Ser Pro Leu Val
                180                 185                 190
Arg Val Lys Glu Glu Pro Pro Ser Pro Pro Gln Ser Pro Arg Val Glu
            195                 200                 205
Glu Ala Ser
        210

<210> SEQ ID NO 4
<211> LENGTH: 206
<212> TYPE: PRT
<213> ORGANISM: Mus musculus

<400> SEQUENCE: 4

His Val Phe Asp Gln Gly Gln Phe Ala Lys Glu Val Leu Pro Lys Tyr
 1               5                  10                  15
Phe Lys His Asn Asn Met Ala Ser Phe Val Arg Gln Leu Asn Met Tyr
                20                  25                  30
Gly Phe Arg Lys Val Val His Ile Glu Gln Gly Gly Leu Val Lys Pro
             35                  40                  45
```

```
Glu Arg Asp Asp Thr Glu Phe Gln His Pro Cys Phe Leu Arg Gly Gln
 50                  55                  60

Glu Gln Leu Leu Glu Asn Ile Lys Arg Lys Val Thr Ser Val Ser Thr
 65                  70                  75                  80

Leu Lys Ser Glu Asp Ile Lys Ile Arg Gln Asp Ser Val Thr Arg Leu
                 85                  90                  95

Leu Thr Asp Val Gln Leu Met Lys Gly Lys Gln Glu Cys Met Asp Ser
                100                 105                 110

Lys Leu Leu Ala Met Lys Leu Ile Ser Leu Val Gln Ser Asn Arg Ile
                115                 120                 125

Leu Gly Val Lys Arg Lys Ile Pro Leu Met Leu Ser Asp Ser Asn Ser
130                 135                 140

Ala His Ser Val Pro Lys Tyr Gly Arg Gln Tyr Ser Leu Glu His Val
145                 150                 155                 160

His Gly Pro Gly Pro Tyr Ser Ala Pro Ser Ala Tyr Ser Ser Ile
                165                 170                 175

Asp Glu Arg Pro Leu Ser Ser Thr Leu Val Arg Val Lys Gln Glu
                180                 185                 190

Pro Pro Ser Pro Pro His Ser Pro Arg Val Leu Glu Ala Ser
                195                 200                 205

<210> SEQ ID NO 5
<211> LENGTH: 195
<212> TYPE: PRT
<213> ORGANISM: Danio rerio

<400> SEQUENCE: 5

His Val Phe Asp Gln Gly Arg Phe Ser Lys Glu Val Leu Pro Lys Tyr
  1               5                  10                  15

Phe Lys His Asn Asn Met Ala Ser Phe Val Arg Gln Leu Asn Met Tyr
                 20                  25                  30

Gly Phe Arg Lys Val Val His Ile Glu Gln Gly Gly Leu Val Lys Pro
                 35                  40                  45

Glu Lys Asp Asp Thr Glu Phe Gln His Pro Tyr Phe Ile Arg Gly Gln
 50                  55                  60

Glu Gln Leu Leu Glu Asn Ile Lys Arg Lys Val Thr Thr Val Ser Asn
 65                  70                  75                  80

Ile Lys His Glu Asp Tyr Lys Phe Ser Thr Asp Val Ser Lys Met
                 85                  90                  95

Ile Ser Asp Val Gln His Met Lys Gly Lys Gln Glu Ser Met Asp Ser
                100                 105                 110

Lys Ile Ser Thr Leu Lys Leu Ile Thr Leu Ala Arg Ser Asn Arg Pro
                115                 120                 125

Leu Met Leu Asn Asp Ser Ser Ser Ala His Ser Met Pro Lys Phe Ser
130                 135                 140

Arg Gln Tyr Ser Leu Glu Ser Pro Ala Pro Ser Ser Thr Ala Phe Thr
145                 150                 155                 160

Gly Thr Asp Glu Trp Ile Glu Asp Arg Thr Ser Pro Leu Val His Lys
                165                 170                 175

Glu Glu Pro Ser Ser Pro Ala His Ser Pro Glu Val Glu Glu Val Cys
                180                 185                 190

Pro Val Glu
195
```

```
<210> SEQ ID NO 6
<211> LENGTH: 200
<212> TYPE: PRT
<213> ORGANISM: Xenopus laevis

<400> SEQUENCE: 6

His Val Phe Asp Gln Gly Gln Phe Ala Lys Glu Val Leu Pro Lys Tyr
 1               5                  10                  15

Phe Lys His Asn Asn Met Ala Ser Phe Val Arg Gln Leu Asn Met Tyr
            20                  25                  30

Gly Phe Arg Lys Val Val His Ile Glu Gln Gly Gly Leu Val Lys Pro
        35                  40                  45

Glu Arg Asp Asp Thr Glu Phe Gln His Pro Tyr Phe Ile Arg Gly Gln
    50                  55                  60

Glu Gln Leu Leu Glu Asn Ile Lys Arg Lys Val Asn Thr Met Ser Ala
65                  70                  75                  80

Thr Lys Ser Asp Glu Val Lys Val Arg Gln Asp Ser Val Gly Lys Leu
                85                  90                  95

Ile Ser Asp Val Gln Ser Met Lys Gly Lys Gln Glu Ser Ile Asp Gly
            100                 105                 110

Arg Leu Leu Ser Met Lys Leu Val Ser Leu Val Gln Ser Asn Arg Ile
        115                 120                 125

Leu Gly Val Lys Arg Lys Ile Pro Leu Met Leu Asn Asp Ser Ser Thr
    130                 135                 140

Gly His Ser Pro Pro Lys Tyr Ser Arg Gln Tyr Ser Leu Glu His Val
145                 150                 155                 160

Pro Ser Ser Thr Ser Tyr Pro Val Ser Gly Phe Thr Asp Ser Leu Glu
                165                 170                 175

Ala Ser Pro Ser Pro Val Ile Leu Ile Lys Thr Glu Pro Leu Thr Pro
            180                 185                 190

Ser Gln Ser Pro Glu Gln Ser Pro
        195                 200

<210> SEQ ID NO 7
<211> LENGTH: 199
<212> TYPE: PRT
<213> ORGANISM: Drosophila

<400> SEQUENCE: 7

His Val Phe Asp Gln Gly Gln Phe Ala Lys Glu Val Leu Pro Lys Tyr
 1               5                  10                  15

Phe Lys His Asn Asn Met Ala Ser Phe Val Arg Gln Leu Asn Met Tyr
            20                  25                  30

Gly Phe Arg Lys Val Val His Ile Glu Gln Gly Gly Leu Val Lys Pro
        35                  40                  45

Glu Arg Asp Asp Thr Glu Phe Gln His Pro Tyr Phe Ile Arg Gly Gln
    50                  55                  60

Glu Gln Leu Leu Glu Asn Ile Lys Arg Lys Val Asn Thr Met Ser Ala
65                  70                  75                  80

Thr Lys Ser Asp Glu Val Lys Val Arg Gln Asp Ser Val Gly Lys Leu
                85                  90                  95

Ile Ser Asp Val Gln Ser Met Lys Gly Lys Gln Glu Ser Ile Asp Gly
            100                 105                 110

Arg Leu Leu Ser Met Lys Leu Val Ser Leu Val Gln Ser Asn Arg Ile
        115                 120                 125

Leu Gly Val Lys Arg Lys Ile Pro Leu Met Leu Asn Asp Ser Ser Thr
    130                 135                 140
```

```
Gly His Ser Pro Pro Lys Tyr Ser Arg Gln Tyr Ser Leu Glu His Val
145                 150                 155                 160

Pro Ser Ser Thr Ser Tyr Pro Val Ser Gly Phe Thr Asp Ser Leu Glu
                165                 170                 175

Ala Ser Pro Ser Pro Val Ile Leu Ile Lys Thr Glu Pro Leu Thr Pro
            180                 185                 190

Ser Gln Ser Pro Glu Gln Ser
        195

<210> SEQ ID NO 8
<211> LENGTH: 237
<212> TYPE: PRT
<213> ORGANISM: Caenorhabditis elegans

<400> SEQUENCE: 8

His Ile Ser Asp Pro Tyr Leu Phe Gly Arg Asn Val Leu Pro His Phe
1               5                   10                  15

Phe Lys His Asn Asn Met Asn Ser Met Val Arg Gln Leu Asn Met Tyr
                20                  25                  30

Gly Phe Arg Lys Met Thr Pro Leu Ser Gln Gly Gly Leu Thr Arg Thr
            35                  40                  45

Glu Ser Asp Gln Asp His Leu Glu Phe Ser His Pro Cys Glu Val Gln
50                  55                  60

Gly Arg Pro Glu Leu Leu Ser Gln Ile Lys Arg Lys Gln Ser Ala Arg
65                  70                  75                  80

Thr Val Glu Asp Lys Gln Val Asn Glu Gln Thr Gln Gln Asn Leu Glu
                85                  90                  95

Val Val Met Ala Glu Met Arg Ala Met Arg Glu Lys Ala Lys Asn Met
            100                 105                 110

Glu Asp Lys Met Asn Lys Leu Thr Leu Val Ser Val Met Gln Pro Gly
        115                 120                 125

Leu Ser Lys Arg Val Ala Lys Arg Gly Val Leu Glu Ile Asp Phe Cys
130                 135                 140

Ala Ala Asn Gly Thr Ala Gly Pro Asn Ser Lys Arg Ala Arg Met Asn
145                 150                 155                 160

Ser Glu Glu Gly Pro Tyr Lys Asp Val Cys Asp Leu Leu Glu Ser Leu
                165                 170                 175

Gln Arg Glu Thr Gly Ser Ala Gln Asp Leu Phe Gly Asp Thr Phe Gly
            180                 185                 190

Ala Gln Ser Ser Arg Tyr Ser Asp Gly Gly Ala Thr Ser Ser Arg Glu
        195                 200                 205

Gln Ser Pro His Pro Ile Ile Ser Gln Pro Ser Asn Ser Ala Gly
210                 215                 220

Ala His Gly Ala Asn Glu Gln Lys Pro Asp Asp Met Tyr
225                 230                 235

<210> SEQ ID NO 9
<211> LENGTH: 74
<212> TYPE: PRT
<213> ORGANISM: Saccharomyces cerevisiae

<400> SEQUENCE: 9

Ile Val Thr Asn Arg Glu Glu Phe Val His Gln Ile Leu Pro Lys Tyr
1               5                   10                  15

Phe Lys His Ser Asn Phe Ala Ser Phe Val Arg Gln Leu Asn Met Tyr
                20                  25                  30
```

-continued

```
Gly Trp His Lys Val Gln Asp Val Lys Ser Gly Ser Ile Gln Ser Ser
            35                  40                  45

Ser Asp Asp Lys Trp Gln Phe Glu Asn Glu Asn Phe Ile Arg Gly Arg
    50                  55                  60

Glu Asp Leu Leu Glu Lys Ile Ile Arg Gln
65                  70
```